United States Patent [19]

Hercend et al.

[11] Patent Number: 5,700,907
[45] Date of Patent: Dec. 23, 1997

[54] NUCLEOTIDE SEQUENCES CODING FOR VARIABLE REGIONS OF β CHAINS OF HUMAN T LYMPHOCYTE RECEPTORS, CORRESPONDING PEPTIDE SEGMENTS AND THE DIAGNOSTIC AND THERAPEUTIC USES

[75] Inventors: Thierry Hercend, Nogant-sur Marne; Frederic Triebel, Versailles; Sergio Roman-Roman, Paris; Laurent Ferradini, Paris, all of France

[73] Assignee: Roussel Uclaf, France

[21] Appl. No.: 423,383

[22] Filed: Apr. 14, 1995

Related U.S. Application Data

[63] Continuation of Ser. No. 934,530, Nov. 23, 1992, abandoned.

[30] Foreign Application Priority Data

| Feb. 12, 1991 | [FR] | France | 91 01613 |
| Apr. 12, 1991 | [FR] | France | 91 04523 |
| Feb. 12, 1992 | [FR] | France | 92 00130 |

[51] Int. Cl.$^6$ .................................................. C07K 14/725
[52] U.S. Cl. ............................................. 530/324; 536/23.5
[58] Field of Search ........................... 435/69.1, 240.2, 435/252.3, 320.1, 325; 530/324, 350; 536/23.5; 514/12

[56] References Cited

PUBLICATIONS

Goverman et al. (1991) Basic and Clinical Immunology, ed. by Stites and Terr. Norwalk, Ct. Appleton and Lange, pp. 73–77.

Chien et al. (1993) Immunology Today, 14, 597–602.

Plaza (1991) Genbank, Locus HSV55RNA, Accession #X57613.

Plaza (1991) Genbank, Locus HS22ARNA, Accession #X57725.

Concannon (1986) Genbank, Locus HUMTCYBC, Accession #M13850, M16302.

George (1990) Genbank, Locus HSTVB55, Accession #X56142.

Plaza (1991) Genbank, Locus HS134BRNA, Accession #X57721.

Plaza (1991) Genbank, Locus HSV56RNA, Accession #X57615.

Ayala et al. (1980) Modern Genetics, Menlo Park, CA: Benjamin/Cummings Co.

Kimura et al (1987) Eur. J. Immunol. 17, 375–383.

Leiden et al. (1986) Immunogenetics 24, 17–23.

Plaza (1991) Genbank, Locus HSV91RNA, Accession #X57614.

Vandenbark et al. (1989) Nature, 341, 541–543.

*Primary Examiner*—John Ulm
*Assistant Examiner*—Karen E. Brown
*Attorney, Agent, or Firm*—Bierman, Muserlian and Lucas LLP

[57] ABSTRACT

The present invention relates to new nucleotide sequences coding for variable regions of β chains of human T lymphocyte receptors, corresponding peptide segments and the diagnostic and therapeutic uses.

6 Claims, 14 Drawing Sheets

FIG. 1

```
Vβ5        -50
IGRb08  GAACTCACTCTGGGTTCTTCCCCAGGAGGACCAAGCCCTGAATCAGGTGCAGTGCTGCCCCACTGTGCAGTGCCTGGGCTCCTCTGCTGGGGTGCTGCTTT
HBP51   ...................................................................T.CA...G....T..........
PH24    ...................................................................CA..GG.A...T..........
IGRb09  ................................................................................CA........

1
IGRb08  GTCTCCTGGGAGCAGGCCCAGTGGACGCTGGAGTCACCCAAAGTCCACACCTGATCAAAACGAGAACGAGCAAGTGACTCTGAGATGCTCCTATCTCTG
VB12A1  .....................................A......T......T....T.........................C...........
HBP51                                    GCAG.ACTG.
PH24                                            AA.G......T....C..A.G.T.T.........A....C....C........
IGRb09                                        A..G..AAGG....G....T..A.G...T........A..G.C....C........
PL2.5                                       TT.....................................................AG.
IGRb06                                                                                              .AG.
                                                      100

IGRb08  AGCACAAGAGTGTCTGGTACCAACAGTCCTGGGTCAGGGGCCCCAGTTTATCTTTCAGTATTATGAAAGAGAGAAGAGAGGAAACTTCCCTGATC
VB12A1  G................................................................................
HBP51   G...T.G..........A...........AC.CA..A.....C.TT......CC....G.A..C.TCAGTG.GAC.C.....AAC.A......G.
PH24    G...T.G..........A...........AC..A..A.....C.TT......CC....G.A..C.TCAGTG.GAC.C.....AAC.A....T.G.
IGRb09  G...TG.C.C.......................C................T...........G.G..............CAG..........
PL2.5   G...TG.C.C.......................C................T..C.T....C.CC..C.C.TG...G.C..CAG..........
IGRb06  G......CC..........A..............C................T..C.T....C.CC..C.C.TG...G.C..GGT..AAC.......CC.A
IGRb07                                                                              AG.G.G......AT..C......CC.A
                                                    200                         300

IGRb08  GATTCTCAGCTCGCCAGTTCCCTAACTATAGCTCTGAGCTGAATGTGAACGCCTTGTTGCTGGGGGACTCGGCCCTGTATCTCTGTGCCAGCAGC  339
VB12A1  ..........................................................................................    264
HBP51   ........GG......T.............C.C..............A......GA..........T.....T..C.............        339
PH24    ........GG......T.............C.C..............A......GA..........T.....T..C........GCT          331
IGRb09  ....G..A..........................................................C............                 339
PL2.5   ....G..A.........................A...............................C............                 234
IGRb06  ...T..G...........T...................................GA.......A.                               238
IGRb07  .....G..T...........T..................................GA.......AC.                             192
```

```
         1
PH27    CAACTTGTGCCCTTTGTCTCCTGTGGACAGGACACATGGATGGATGCTGGAATCACCC
PL4.2
IGRb13                  T........G....----....A........

100
PH27    AGAGCCCAAGACACAAGGTCACAGAGACAGGAACACCAGTGACTCTGAGATGTCACCA
PL4.2                                ............................
IGRb13  ................A................GG.AG.....CT..GCG........

PH27    GACTGAGAACCACCGCTATATGTACTGGTATCGACAAGACCCGGGGCATGGGCTGAGG
PL4.2   .......................C...................................
IGRb13  ....TG.......AA.A......T................T...A............

200
PH27    CTGATCCATTACTCATATGGTGTTAAAGATACTGACAAAGGAGAAGTCTCAGATGGCT
PL4.2   ..A........................................................
IGRb13  .....................C....C...A............................

PH27    ATAGTGTCTCTAGATCAAAGACAGAGGATTTCCTCCTCACTCTGGAGTCCGCTACCAG
PL4.2   ........................................................-......
IGRb13  .C............C.......CC...C..............T...G..TC

300
PH27    CTCCC-AGACATCTGTGTACTTCTGTGCCATCAGC  324
PL4.2   .....G.....................CT..A     237
IGRb13  .....-........A..T.....C....G...G    294
```

```
         1
IGRb14 AGAAGACCCCTCCATCCTGTAGCACCTGCCATGGAGCATCGGGCTCCTGTGCTGTGGCCTTTTCTCTCTGTGGGCAAGTCCAGTGAATGCTGGTGT
IGRb15 .........TG.T..........T.......A..A............................G...........T......GA.
IGRb16 ..............................................................................
HBVP34                            aaggcccagcccctttccattggggctgcagcatcagctgtttccttctctgcag.........
CEM    ..............................................................CA...G...........G.
         ...CG..TT...........C................................................................

IGRb14 CACTCAGACCCCAAAATTCCAGTCTCCTGAGACACAGAGCATGACACTGCAGTGTGCCCAGGATATGAACCATACTCCATGTACTGGTATCGAC
IGRb15 ....C...G.A....C..CT..A....GCAG.....G.C.........AGA..A..........GA.....TG........A.........
IGRb16 ........................GCA.................T.................................................
HBVP34 .............................................................................G.A.A......
CEM    .........................G........................T..........................G.A.A......

200
IGRb14 AAGACCCAGGACATGGAGCTGAGGCTGATTATTACTCAGCTTCTGAGGGTACCACTGACAAAGGAGAAGTCCCATGGCTACAATGTCTCCAGATTA
IGRb15 ....T..T..AC...G.A....C..CC..T..AA..A..CA.........G..........T...........TG...T..TG...GC......
IGRb16 ..............G..A......T....T.GG..CT...T.........CT.............C.............G.....C......
HBVP34 ............G...................T.GG..CT....T.........CT.........A.....C......................
CEM    ...........-G....................T.GG........................G.....C........G.....TG..........

300
IGRb14 AACAAACGGGAGTTCTCGCTCAGGCTGGAGTCGGCTGCTCCTCCCCAGACATCTGTGTACTTCTGTGCCAGCACC  339
IGRb15 ..C.GAT..T...C.C....C.T..........T....TA....T..............................GT  339
IGRb16 ..C..C.GA..T...C............T..................................................GT  345
HBVP34 ..C..C.GA..T...C.............CT.......................................................GT  339
CEM    ...A.....A..A..T....CT.......GG..T................A...........................G....  339
```

```
        1
IGRb17  GACCCCAGTCAGAGAGCCCCATCTCAGACCCGAGGCTAGCATGGGCTGCAGGCTGCTCTGCTGTGCGGTTCTCTGTCTCCTGGGAGCCGGTCCCATGGAAA
IGRb18  ............................................................................................A.T.....A..C.
IGRb19  .............................................................................................

100
IGRb17  CGGGAGTTACGCAGAGACACCAAGACACCTGGTCATGGGAATGACAAATAAGAAGTCTTTGAAATGTGAACAACATCTGGGGCATAACGCTATGTATTGGTA
IGRb18  ..............C.......A................................T...........................A....C.GG.......
IGRb19  ..T.A.........C...........................................................................A....C.GG...A.....
PL4.9

200
IGRb17  CAAGCAAAGTGCTAAGAAGCCACTGGAGCTCATGTTTGTCTACAACTTTAAAGAACAGAAAAACAGTGCCAAGTGCTTCTCACCTGAATGC
IGRb18  ..................................................GTC..G......G.GT.................
PL4.19  .....................................................................T.CGCT.C....G..
IGRb19  ..............G.AA...........................C............G..A.G.GA...TCT..AT...TG.A..
VPL4.9  ..............G.AA...........................C............G..A.G.GA...TCT..AT...TG.A..

300
IGRb17  CCCAACAGCTCTCACTTATGCCTTCACCTACAACACCCTGCAGCCAGAGACTCGGCCGCCTGTATCTCTGTGCCAGCACC  339
IGRb18  ................C..............................................C......G.  339
PL4.19  ................T...........................A..G..............C......G.  108
IGRb19  .........G.AA........T....AA.................A.................C......G.  339
PL4.9   .........T.AA........T....AA.................A.................C......G.  255
```

IGRb20 ATCCTGCCCTGGGCCTTGCCTGCTGGTCTGCCTCACTCTGGTCTGCCATGGGCTGCAGGCTCCTCTGCTGTGTGGTCTTCTGCCTCCTCCAAGCAGGTCCCTTGGACA

IGRb20 CAGCTGTTTCCCAGACTCCAAAATACCTGGTCACACAGATGGGAAACGACAGTCCATTAAATGTGAACAAAATCTGGGCCATGATACTATGTATTGGTA
PL2.6  ...........................................................G.T.......................................

IGRb20 TAAACAGGACTCTAAGAATTTCTGAAGATAATGTTTAGCTACAATAATAAGGAGCTCATTATAAATGAAACAGTTCCAAATCGCTTCTCACCTAAATCT
PL2.6  ......................................................................................................

IGRb20 CCAGACAAAGCTCACTTAAATCTTCACATCAATTCCCTGGAGCTTGGTGACTCTGCTGTGTATTTCTGTGCCAGCAGC 339
P12.6  .............................................................................246

FIG. 6

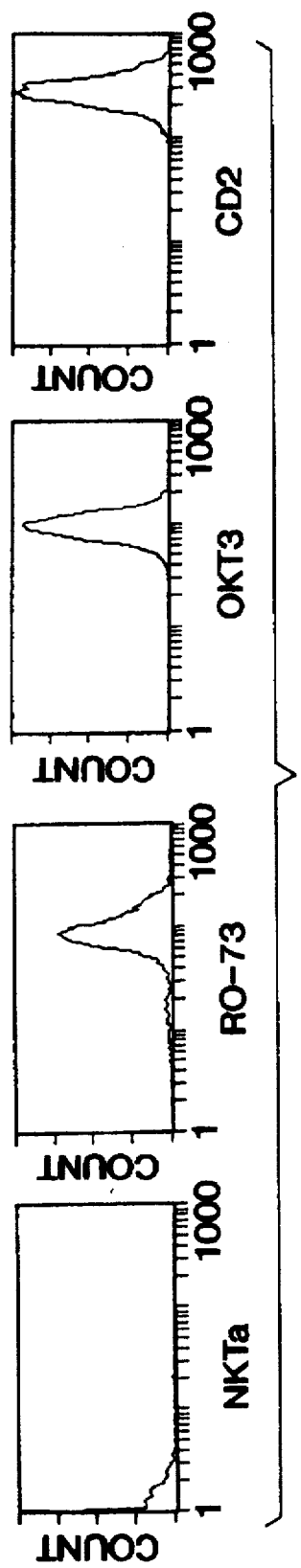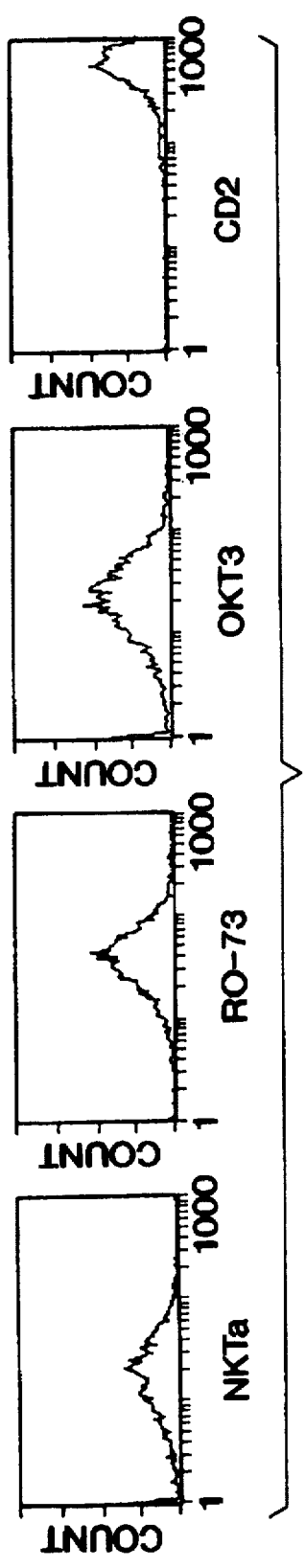

NUCLEOTIDE SEQUENCES CODING FOR VARIABLE REGIONS OF β CHAINS OF HUMAN T LYMPHOCYTE RECEPTORS, CORRESPONDING PEPTIDE SEGMENTS AND THE DIAGNOSTIC AND THERAPEUTIC USES

PRIOR APPLICATION

This application is a continuation of U.S. patent application Ser. No. 934,530 filed Nov. 23, 1992, now abandoned.

The present invention relates to new nucleotide sequences coding for variable regions of β chain T-cell receptors, corresponding peptide segments and the diagnostic and therapeutic uses.

It is known that the receptors recognizing antigens at the surface of mature T lymphocytes (hereafter designated T-cell receptors) possess a structure having a certain similarity with those of immunoglobulins. Therefore, they contain heterodimeric structures containing α and β glycoprotein chains or γ and δ glycoprotein chains (see Meuer et al. (1), Moingeon et al. (2), Brenner et al. (3), Bank et al. (4)).

The directory of T-cell receptors must be able to address the immense diversity of antigenic determinants. This is obtained by genetic recombination of different discontinuous segments of genes which code for the different structural regions of T-cell receptors. Thus, the genes contain V segments (variable segments), optionally D segments (diversity segments), J segments (junction segments) and C segments (constant segments). During the differentiation of T-cells, specific genes are created by recombination of V, D and J segments for the β and δ loci and V and J segments for the α and β loci. These specific combinations as well as the pairing of two chains create the combinational diversity. This diversity is highly amplified by two supplementary mechanisms, namely the imprecise recombination of V-D-J or V-J segments and the addition of nucleotides corresponding to the N region (Davis et al. (5)).

A certain number of genetic V segments are already known. These segments have been grouped into subfamilies as a function of the similarity of sequences. By definition, the segments which have more than 75% similarity in the nucleotide sequence have been considered as members of the same subfamily (Crews et al. (6)). At present, about 60 distinct Vβ genetic segments are known (Wilson et al. (7), Robinson (8), Leider et al. (9), Reynolds (10), Li et al. (11)) which have been classified into 20 subfamilies, 7 of which have only one member (see Wilson et al. already quoted).

Furthermore, monoclonal antibodies directed against specific segments of the variable parts of T-cell receptors, in particular the β or δ chains, were recently described in WO 90/06758. These monoclonal antibodies are useful not only as diagnostic tools but also as therapeutic tools, for example, vis-à-vis rheumatoid athritis.

The use of synthetic peptides corresponding to the variable regions of the α or β chains in the treatment of auto-immune diseases was also described (27 and 28).

It is also known that variations exist from one individual to another in the expression of different variable segments of the T-cell receptor in man (27 and 28).

The present invention aims to enrich the directory of genetic segments coding for the variable regions of the β chains of T-cell receptors by providing new Vβ genetic segments belonging to new subfamilies or belonging to subfamilies of which at least one member is already known.

Therefore a subject of the present invention is nucleotide sequences coding for the variable regions of β chains of human T lymphocyte receptors, corresponding no cDNAs containing nucleotide sequences chosen from any one of the Vβ segments corresponding to one of the sequences SEQ ID No. 2 to 19, and the sequences which differ from them by one or more nucleotides.

More particularly a subject of the present invention is: sequences coding for the variable regions of β chains of human T lymphocyte receptors, corresponding to cDNAs containing nucleotide sequences chosen from any one of the Vβ segments corresponding to one of the sequences SEQ ID No. 2 to 5, and the sequences which differ from them by one or more nucleotides.

The expression "and sequences which differ from them by one or more nucleotides", encompasses alleles which differ by up to 8 nucleotides, but more often differ by 1 or 2 nucleotides, or which can differ by the deletion or addition of one or two codons.

Also a more particular subject of the invention is:

nucleotide sequences coding for the variable regions of β chains of human T lymphocyte receptors, corresponding to cDNAs corresponding to all or part of the nucleotide sequences chosen from any one of the Vβ segments corresponding to one of the sequences SEQ ID No. 2 to 5, and the sequences which differ from them by one or two nucleotides, nucleotide sequences coding for the variable regions of the β chains of human T lympkocyte receptors, corresponding to cDNAs corresponding to one of the nucleotide sequences chosen from any one of the Vβ segments corresponding to one of the sequences SEQ ID No. 6 to 15, the sequences which differ from them by one or two nucleotides and fragments of the latter, in particular, the fragments of sequences which correspond to all or part of the nucleotide sequences chosen from any one of the V segments corresponding to one of the sequences:

1 to 155 of SEQ ID No. 8
1 to 125 of SEQ ID NO. 9
1 to 111 of SEQ ID No. 10 and the sequences which differ from them by one or two nucleotides, nucleotide sequences coding for the variable regions of the β chains of human T lymphocyte receptors, corresponding to cDNAs corresponding to all or part of the nucleotide sequences chosen from any one of the Vβ segments corresponding to one of the sequences:

1 to 195 of SEQ ID No. 16
1 to 99 of SEQ ID No. 17
1 to 113 of SEQ ID No. 18
1 to 186 of SEQ ID No. 19, and the sequences which differ from them by one or two nucleotides.

By the expression "nucleotide sequences corresponding to cDNAs corresponding to all or part of the nucleotide sequences" is also designated the complete sequences as well as fragments of these sequences, including short fragments which can be used as probes (generally containing at least 10 nucleotides) or as primers (generally containing at least 15 nucleotides). In a general fashion, the present invention encompasses the group of new oligonucleotides which are fragments of Vβ sequences according to the invention.

As for the sequences which differ by one or two nucleotides, they correspond to variations which are observed experimentally at the time of determination of the nucleotide sequence of several cDNAs.

Also a subject of the present invention is the peptides coded by the nucleotide sequences according to the invention as well as the alleles and the derivatives of the latter which have the same function.

In a general fashion, the present invention encompasses the peptides constituted by or composed of a peptide sequence coded by the nucleotide sequences according to the invention as well as fragments of these peptides. It also encompasses the peptides which differ from the latter by one or more amino acids and which have the same function. These peptides can correspond to modifications such as those known with muteins or to allelic variations. In fact it has been shown in particular that certain genetic segments coding for the variable regions of chains of T receptors in man were subjected to a phenomenon of genetic polymorphism called allelic variation (29). The present invention encompasses the peptides resulting from this phenomenon.

The nucleotide sequences according to the invention have been obtained according to the following stages:
- isolation of the RNAs of peripheral lymphocytes of an individual;
- obtaining the complementary DNA using reverse transcriptase and a primer A which is specific to the C$\beta$ region (SEQ ID No. 20);
- genetic amplification (by Anchored Polymerase Chain Reaction or A-PCR) using a DNA polymerase, a poly C primer (SEQ ID No. 21) and a primer B which is specific to the C$\beta$ region (SEQ ID No. 22);
- a new amplification by A-PCR using DNA polymerase and a primer C which is specific to the C$\beta$ region (SEQ ID No. 23);
- insertion in a plasmid vector;
- transformation of a bacterial host with the recombinant vector;
- screening of recombinant bacterial colonies with a labelled oligonucleotide D which is specific to C$\beta$ (SEQ ID No. 24);
- extraction of plasmids from positive colonies;
- and sequencing of DNA fragments containing the C$\beta$ region.

The present invention can be reproduced, in particular, by bispecific genetic amplification (polymerase chain reaction or PCR) by starting with the peripheral lymphocytes which express the mRNAs including the variable or junctional $\beta$ segments corresponding to sequences ID No. 2 to 19 of the invention or alternatively by applying this PCR technique to genomic DNA of any somatic cell of an individual taken at random. The invention can also be reproduced by preparing the above genetic sequences by the chemical synthesis of oligonucleotides.

The peptides according to the invention can be obtained by standard peptide synthesis. They can also be obtained by the application of known genetic engineering techniques including the insertion of a DNA sequence coding for a peptide according to the invention into an expression vector such as a plasmid and the transformation of cells with this expression vector.

Therefore a subject of the present invention is also plasmids and expression vectors containing a DNA sequence coding for a peptide according to the invention as well as the hosts transformed with this vector.

Also a subject of the present invention is antibodies, and, in particular, monoclonal antibodies, directed against an antigenic determinant belonging to or composed of a peptide according to the invention.

The monoclonal antibodies may be obtained by any of the techniques which allow the production of antibody molecules from cell line culture. These techniques include different techniques using hybridomas.

The antibody production may be obtained in animals by the immunization of the animals by injection with the peptides or fragments according to the invention, whether they be natural, recombinant or synthetic, optionally after coupling to an immunogen such as tetanus anatoxin, or also by injection of human T lymphocytes expressing the corresponding sequences at their surface, including recombinant cells transfected with the corresponding coding sequences.

Also a subject of the present invention is hybridomas producing monoclonal antibodies directed against the polypeptides according to the invention.

The present invention also encompasses the fragments and the derivatives of monoclonal antibodies according to the invention which are reactive with defined variable regions of T-cell receptors. These fragments are, in particular, the F(ab')$_2$ fragments which can be obtained by the enzymatic cleavage of antibody molecules with pepsin, the Fab' fragments which can be obtained by reduction of the disulphide bridges of F(ab')$_2$ fragments and the Fab fragments which can be obtained by the enzymatic cleavage of antibody molecules with papain in the presence of a reducing agent. The fragments can also be obtained by genetic engineering.

The monoclonal antibody derivatives are for example antibodies or fragments of these antibodies to which labellers such as a radio-isotope are attached. The monoclonal antibody derivatives are also antibodies or fragments of these antibodies to which therapeutically active molecules are attached, in particular, cytotoxic compounds.

The products of the invention have several uses in the field of diagnostics and in the field of therapeutics.

1—Uses in the field of diagnostics

The oligonucleotides contained in the nucleotide sequences according to the invention can be used to constitute detection probes (generally at least 10 nucleotides) which are capable of hybridizing with a variable region of a $\beta$ chain or primers for the amplification of DNA (generally containing at least 15 nucleotides and preferably at least 17 nucleotides) which are capable of being linked to a sequence to be amplified.

Thus the oligonucleotides can be used in the diagnosis of immune disorders by detecting the presence of nucleic acid sequences which are homologues of a gene coding for the variable regions of $\beta$ chains of T-cell receptors in the mRNA of a sample from a patient. Different methods can be used to establish a connection between the expression of T-cell genes and an illness. These methods include:

a—the production and analysis of cDNA expression libraries obtained from T-cells connected with the illness to determine the frequency of dominant genes;

b—Southern blot analysis of samples of genomic DNA to determine whether genetic polymorphisms or rearrangements of the genes coding for the T-cell receptors exist;

c—the analysis of samples by obtaining cDNA, amplification by PCR and hybridization with labelled probes;

d—the hybridization in situ of T-cells without culture of T-cells beforehand.

The primers can be used in PCR reactions in a method such as that defined in c.

The monoclonal antibodies, the fragments or the derivatives of these antibodies according to the invention can be used to study T-type immune responses, for example in the field of the auto-immune diseases of cancerology, of allergies, of transplants and of infectious diseases. In particular, the directory of different variable β segments of the T receptor can be studied, whether it be blood or tissue T-cells. In a general fashion the techniques used can be in vitro or in vivo methods.

With in vitro methods, the samples used can be samples of body fluids or tissue samples. The techniques used can include in particular flow cytofluorimetry to analyse blood T lymphocytes or labelling with immunoperoxidase on an anatomopathological section to study the lymphocytes infiltrating the tissues.

With in vivo methods, the antibodies, their fragments or their derivatives are administered by the usual routes, for example by intravenous route, and the immunospecific linkages are detected. This can be obtained for example in the case where an antibody is used which is labelled with a radio-isotope.

2—Uses in the therapeutic field

The oligonucleotides contained in the nucleotide sequences according to the invention can be used in therapeutics as anti sense oligonucleotides. In fact it is known that it is possible in vitro to inhibit the expression of a transcript gene in human lymphocytes by incubating these lymphocytes with an anti sense oligonucleotide specific to the gene in question (30). These anti sense oligonucleotides generally contain at least 10 and, preferably, at least 16 nucleotides. These anti sense oligonucleotides can be in particular the inverted and complemented sequences corresponding to 20 nucleotides upstream from the initiation site of the translation (ATG). The significance of the use in vitro of anti sense oligonucleotides specific to a Vβ genetic segment is to abolish (or strongly diminish) the expression of a T receptor containing this Vβ segment and thus to obtain a phenomenon of clonal deletion at the level of the specific reactivity of T lymphocytes. The anti sense oligonucleotides can not only be used in vitro on human T lymphocytes which are then reinjected, but also in vivo by local or systemic injection preferably after modification to increase the stability in vivo and the penetration into the lymphocytes of these oligonucleotides.

The monoclonal antibodies according to the invention can be used to modulate the immune system. It is in this way that the antibodies can be administered to block the interaction of the effector T-cells with their specific antigen. Anti T receptor antibodies linked for example to a cytotoxic molecule or a radio-isotope can also be administered so as to obtain a clonal deletion, thanks to the specific fixation on a β chain of a T-cell receptor. The monoclonal antibodies according to the invention can be used in therapeutics at low mitogenic concentrations so as to activate, in a specific fashion, certain sub-assemblies of T-cells or can be used at much higher concentrations to fix them to the receptors concerned and thus label these sub-assemblies with a view to their elimination by the reticulo-endothelial system. An important criterion in the treatment of an illness is the ability to modulate the sub-assemblies of T-cells linked with an illness. The exact nature of this therapeutic modulation, namely blocking or suppressing a particular sub-assembly of T-cells or on the contrary stimulating and activating a particular sub-assembly, will depend on the illness in question and the specific sub-assembly of T-cells concerned.

This type of treatment has an advantage over current treatments using antibodies such as the treatment with anti CD3 antibodies in patients having had a kidney transplant and having a rejection problem, given that thanks to the invention there will be no modulation of the totality of the T-cell population but only of the sub-assembly of T-cells expressing the β sub-family specific to the T-cell receptors.

Moreover, as the response of T-cells is often oligoclonal, it is generally convenient to use "cocktails" of several antibodies in therapeutics.

In addition anti Vβ antibodies can be used to select T lyphocytes in vitro, for example by passing through a column containing spheres carrying the antibody. This separation of certain T lymphocytes can be used with a view to culturing these lymphocytes before reinjection into the patient.

Moreover, all or part of the peptide sequences according to the invention can be used in therapeutics, that is to say the peptide sequences coded by the nucleotide sequences according to the invention or fragments of these sequences (generally containing at least 8 to 10 amino acids). These sequences or fragments, administered to humans or animals, can act as a decoy, that is to say they fix themselves on the epitope carried by the harmful antigen and stop the reaction of normal T-cells with the antigen, preventing in this way the development of an illness which is aggressive towards the self determinants. They can also be used as immunogens in the manufacture of vaccines (optionally after conjugation with protein carriers).

BRIEF DESCRIPTION OF THE DRAWINGS

FIG. 1 shows in a line both known Vβ5 sequences and partial sequences according to the invention marked IGRb08 (SEQ ID No. 8), IGRb09 (SEQ ID No. 9), IGRb06 (SEQ ID No. 6) and IGRb07 (SEQ ID No. 7) belonging to known Vβ5 sub-family. In this figure, the numbering of nucleotides starts at the ATG initiation codon (which is underlined). The dots indicate identical nucleotides. The sequence which is assumed to be the leader sequence has a line over it.

FIGS. 2 and 2A shows in a line both known Vβ6 sequences and partial sequences of new sequences according to the invention marked IGRb11 (SEQ ID No. 10) and IGRb12 (SEQ ID No. 11) belonging to known Vβ6 sub-family. In the figure, the numbering of nucleotides starts at the ATG initiation codon (which is underlined). The dots indicate identical nucleotides.

FIG. 3 shows in a line both known Vβ12 sequences and partial sequence of new sequence according to the invention marked IGRb13 (SEQ ID No. 12) belonging to known Vβ12 sub-family. In this figure, the numbering of nucleotides starts at the 5' end of PH27. The dots indicate identical nucleotides. The sequence which is assumed to be the leader sequence has a line over it.

FIG. 4 shows in a line both known Vβ13 sequences and partial sequences of new sequences according to the invention marked IGRb14 (SEQ ID No. 13), IGRb15 (SEQ ID No. 14) and IGRb16 (SEQ ID No. 15) belonging to known Vβ13 sub-family. In this figure, the numbering of nucleotides starts at the ATG initiation codon (which is underlined). The dots indicate identical nucleotides. The sequence which is assumed to be the leader sequence has a line over it.

FIG. 5 shows in a line both known Vβ7 sequences and partial sequences of new sequences according to the invention marked IGRb17 (SEQ ID No. 16), IGRb18 (SEQ ID No. 17) and IGRb19 (SEQ ID No. 18) belonging to known Vβ7 sub-family. In this figure, the numbering of nucleotides starts at the ATG initiation codon (which is underlined). The dots indicate identical nucleotides. The sequence which is assumed to be the leader sequence has a line over it.

FIG. 6 shows in a line both known Vβ9 sequence and partial sequence of new sequence according to the invention marked IGRb20 (SEQ ID No. 19) belonging to known Vβ9 sub-family. In this figure the number of nucleotides starts at the ATG initiation codon (which is underlined). The dots indicate identical nucleotides. The sequence which is assumed to be the leader sequence has a line over it.

Figure 7:
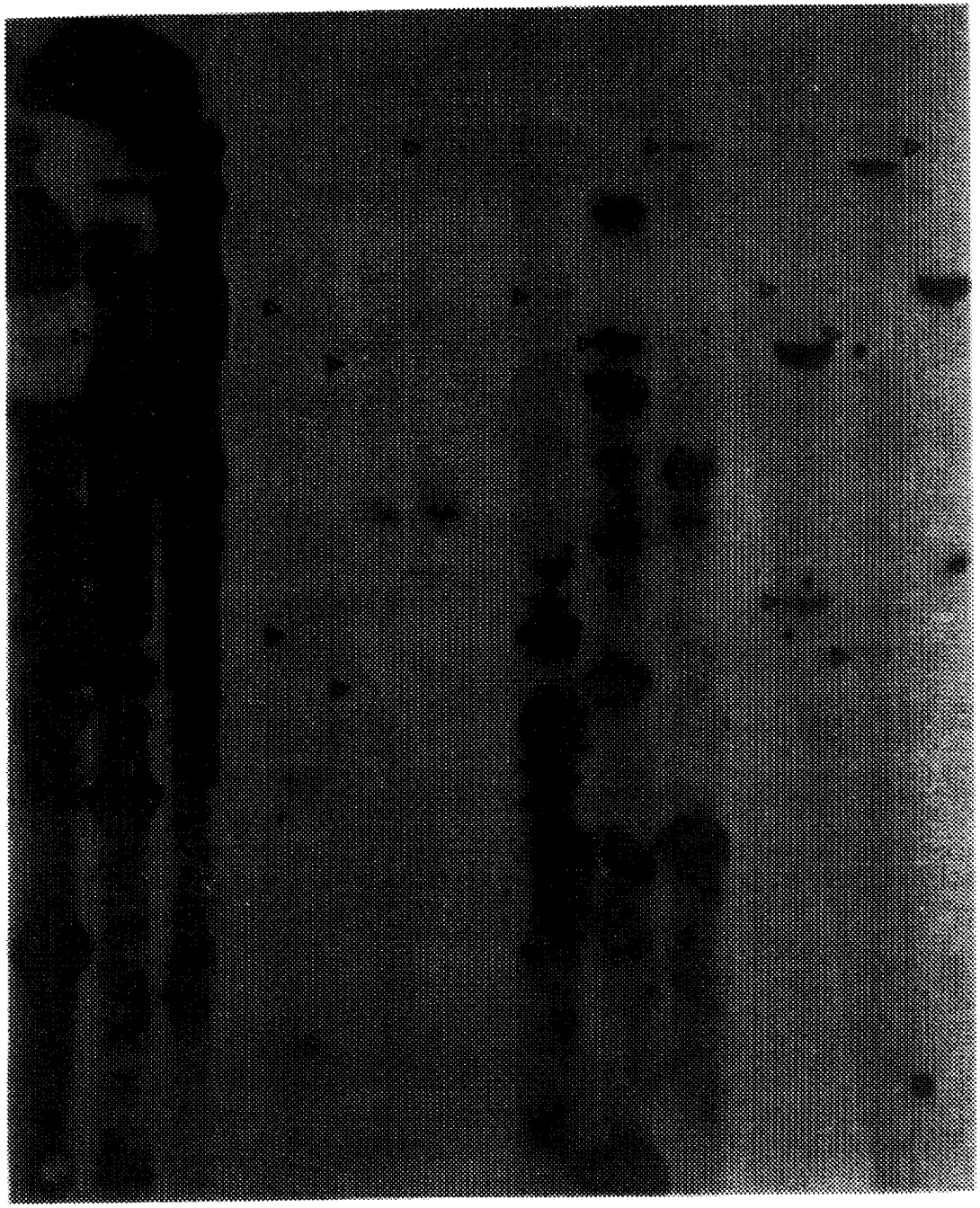

FIG. 7 shows the Southern blot analyses of the genomic DNA treated with a restriction enzyme using probes specific to Vβ sub-families. The restriction enzymes used are EcoRI (column R), Hind III (column H) and Bam I (column B). On this figure the triangles mark the position of DNA fragments hybridizing in a specific fashion with Cβ.

Figure 8:

FIG. 8 represents the detection by autoradiography of amplified transcripts of TCRβ chains expressed by the peripheral lymphocytes of a healthy individual and of a co-amplified β-actin control.

FIGS. 9(A–C) represents the analysis by cytofluorimetry of the reactivity of the monoclonal antibody RO-73 vis-à-vis the immunizing clone 3025 (9A), clone 12410 (9B) and circulating lymphocytes (9C) respectively.

The reactivity-control for NKTa or OKT$_3$ antibodies is given for each type of cell respectively.

The number of cells counted (linear scale) is given as a function of the intensity of fluorescence (logarithmic scale).

Figure 9A:
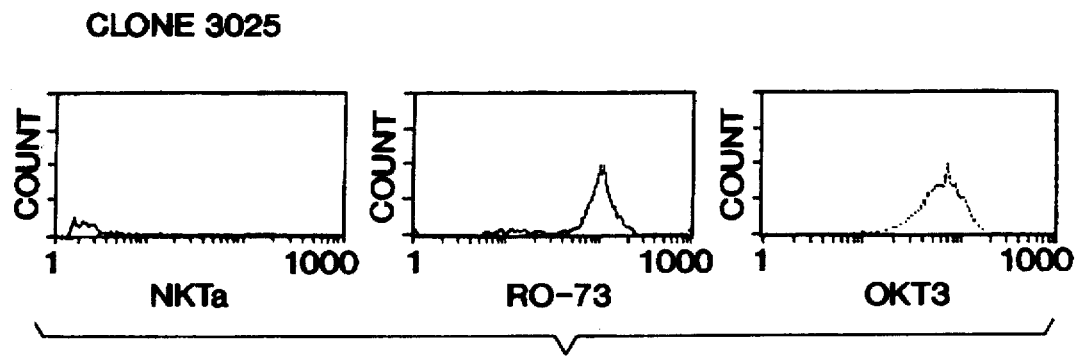
Figure 9B:
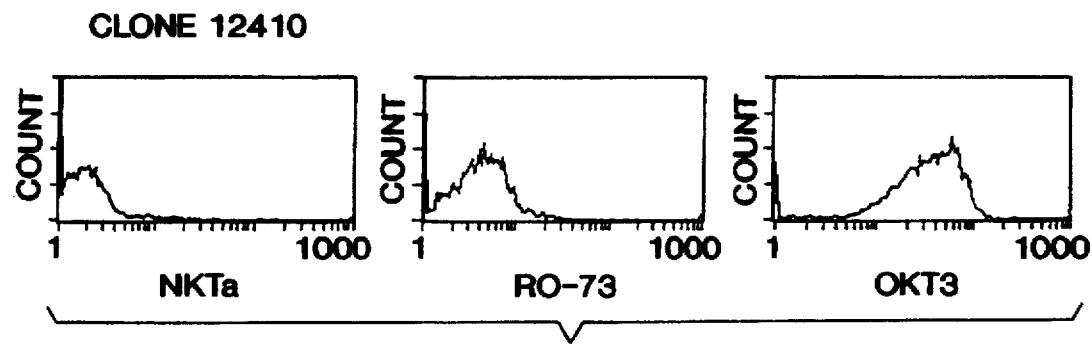
Figure 9C:
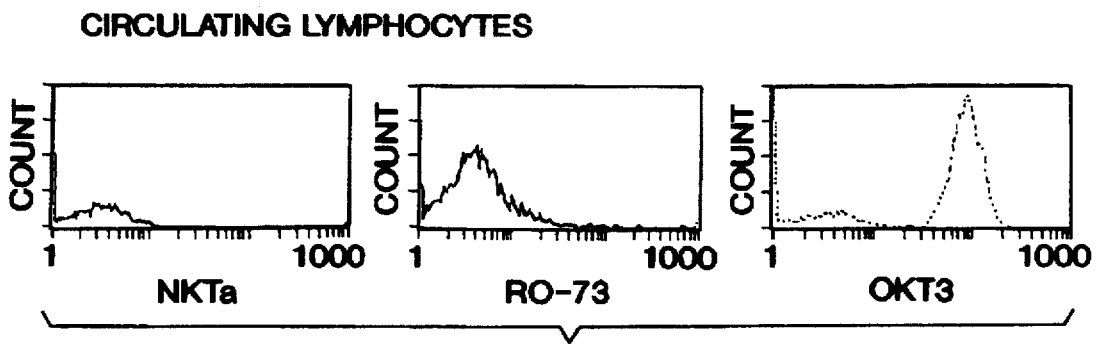
Figure 10A:
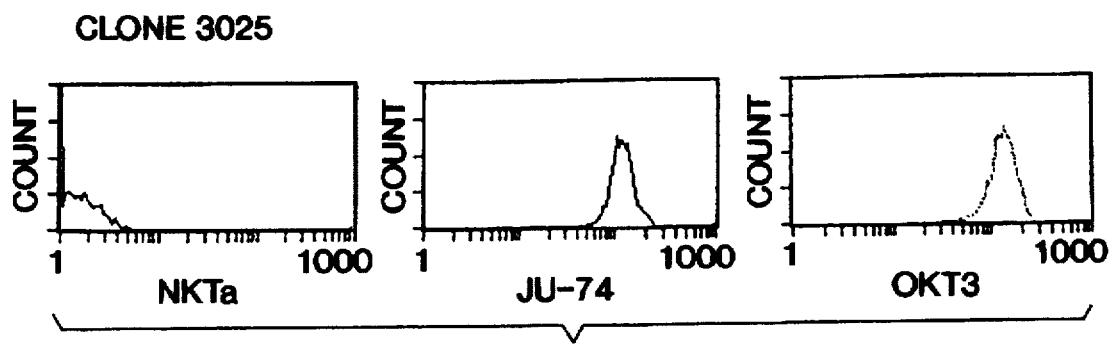
Figure 10B:
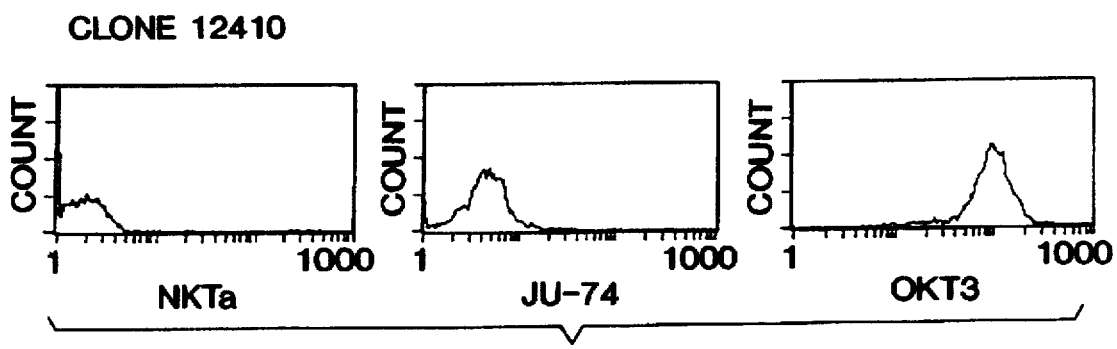
Figure 10C:
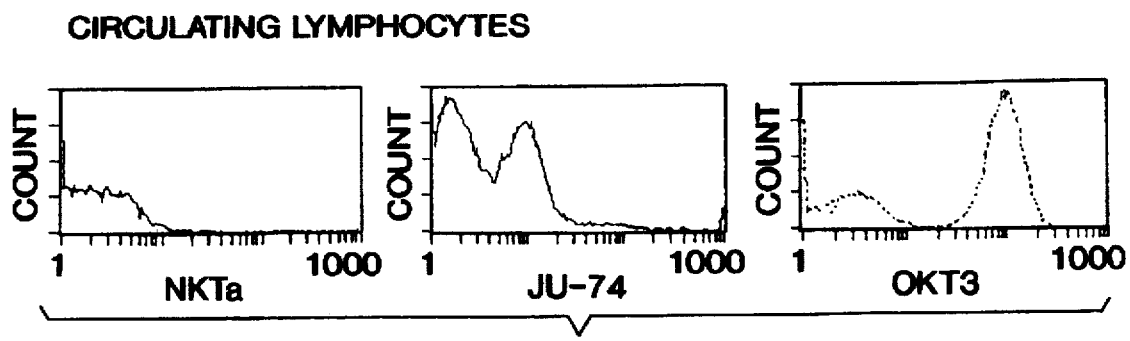

FIGS. 10(A–C) represents the analysis by cytofluorimetry of the reactivity of the monoclonal antibody JU-74 (FIGS. 10A, 10B, 10C: same conditions as for FIGS. 9A, 9B, 9C).

FIGS. 11(A and B) represents the analysis by cytofluorimetry of the comodulation with the CD3 molecule of the TCR structure of clone 3025 recognized by the monoclonal antibody RO-73 respectively in the absence (FIG. 11A) or in the presence of anti-CD3 antibodies (FIG. 11B).

The comodulation-control is given with the monoclonal antibodies NKTa, OKT3 and anti-CD2 respectively.

Figure 12A:
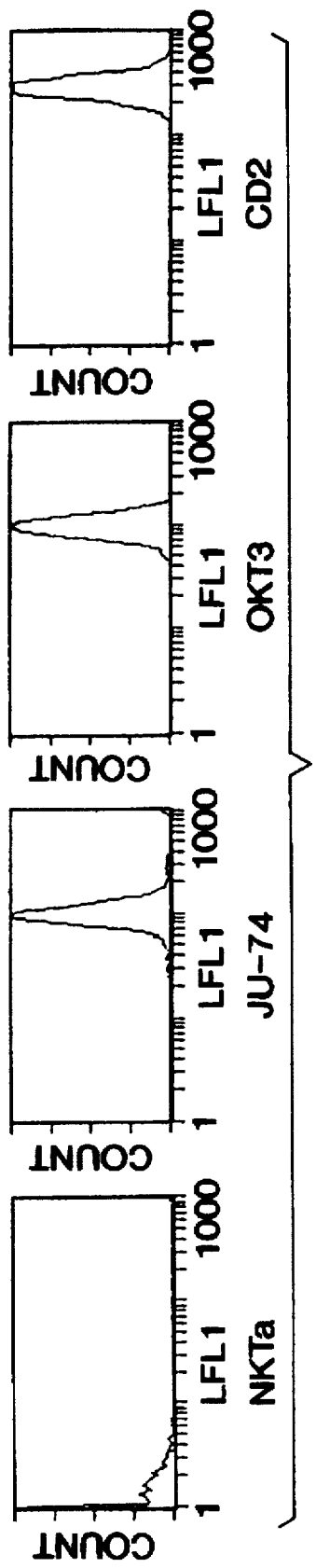
Figure 12B:
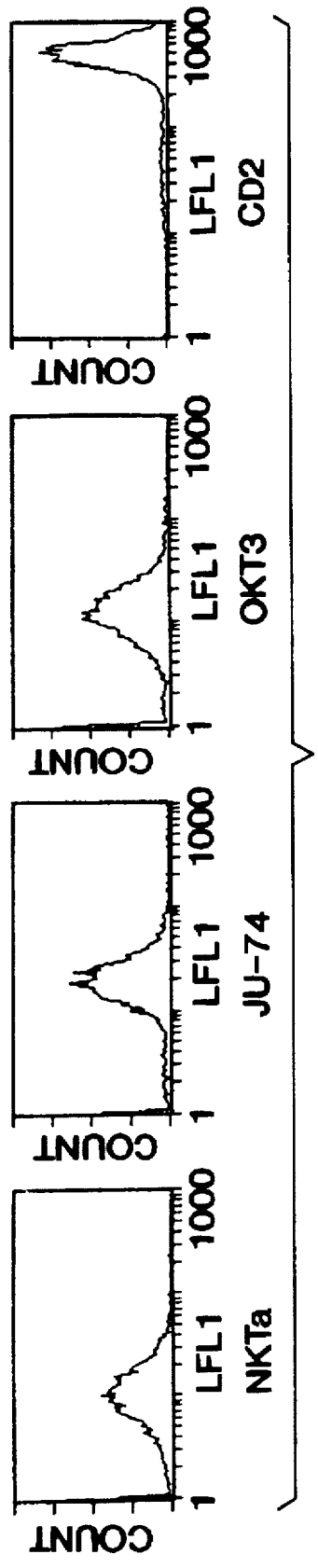

FIGS. 12(A and B) represents the analysis by cytofluorimetry of the comodulation with the CD3 molecule of the TCR structure of clone 3025 recognized by the monoclonal antibody JU-73, respectively in the absence (FIG. 12A) or in the presence of anti-CD3 antibody (FIG. 12B).

Figure 13A:
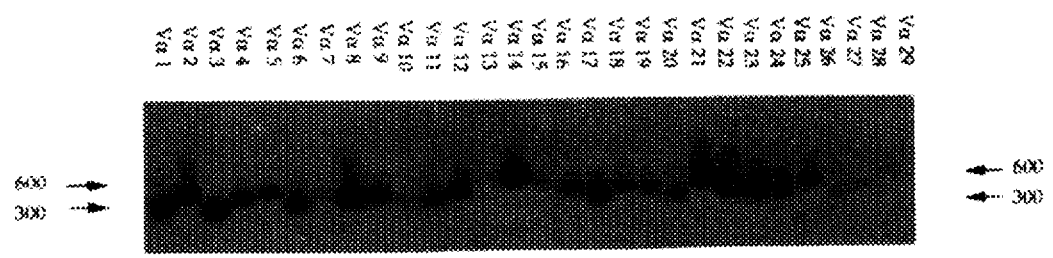
Figure 13B:
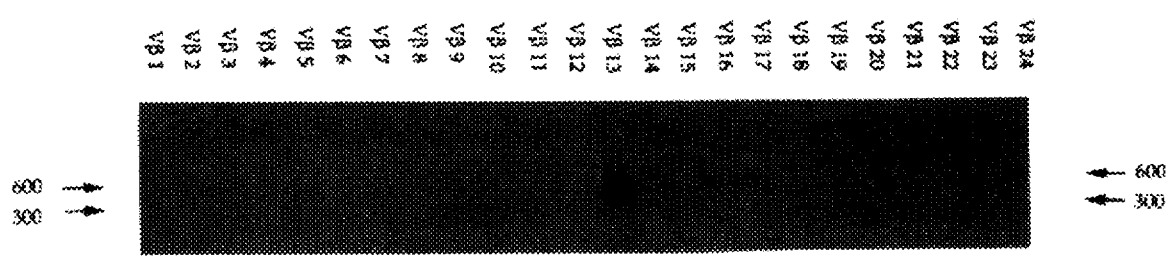

FIGS. 13(A and B) represents the detection by autoradiography of amplified transcripts of TCRα chains (FIG. 13A) and β chains (FIG. 13B) expressed by the RO-73$^+$ cells.

I—Obtaining the cDNA and amplification by PCR

The peripheral lymphocytes of an individual are used as the DNA source. The total RNA was prepared according to the method using guanidinium isothiocyanate and caesium chloride (Chirgwin (12)) or according to a one-stage method by extraction with guanidinium isothiocyanate, phenol and chloroform (Chomcyznski (13)).

The first cDNA strand was synthesized in a final volume of 50 microliters at a temperature of 42° C. for 1 hour using 5 micrograms of total RNA, reverse transcriptase and a primer A which is specific to the Cβ region constituted by the sequence 5'-TATCTGGAGTCATTGAGGGCGGGC (SEQ ID No. 20). This material was then purified by extraction with phenol/chloroform and precipitation with ammonium acetate. After selecting a 0.45/1 kb fraction on agarose gel, the addition of a dG end is carried out on the RNA/cDNA hetero complex in a CoCl$_2$ addition buffer with 14 units of terminal deoxynucleotidyl transferase (TdT) for 30 minutes at 37° C. The reaction was stopped by maintenance at 70° C. for 10 minutes. 1N NaOH (⅓ volume) was added and the sample was incubated at 50° C. for 1 hour to hydrolyze the RNA, then neutralized with Tris HCl 2M pH 8 and 1N HCl. After extraction with a phenol/chloroform mixture the first cDNA strand at end G was precipitated with ethanol and subjected to an amplification using the PCR technique (Polymerase Chain Reaction described by Saiki et al. (14)) in a final volume of 100 microliters containing 50 mM of KCl, 10 mM of Tris-Cl pH 8.3, 1.5 mM of MgCl$_2$, 0.1% (weight/volume) of gelatine, 200 micromoles of dNTP, 2.5 units of Taq polymerase and 100 picomoles of two primers. The two primers used are, on the one hand a poly-C primer (5'-GCATGCGCGCGGCCGCGGAGG-14C) (SEQ ID No.21) described by Loh et al. (15) as well as a primer B specific to the Cβ region (5'-TGTGGCCAGGC ATGCCAGTGTGGCC) (SEQ ID No. 22).

25 amplification cycles are carried out followed by a final 15 minute elongation period at 72° C. Each cycle includes a denaturation stage at 92° C. for 1 minute, a hybridization stage at 55° C. for 2 minutes and an elongation period at 72° C. for 4 minutes. The amplified products are then precipitated with ethanol, resuspended in 30 mM of sodium acetate pH 5, 50 mM NaCl, 1 mM ZnCl$_2$, glycerol 5% by volume and ⅒ of this material is purified as a function of size on a 1% low melting point agarose gel.

A second amplification phase is then carried out directly on approximately 10% of the band containing the agarose following the same conditions as previously, except that the primer 5'-GGTGTGGGAGAATTCTGCTTCTGA (SEQ ID No. 23) is used as primer C which is specific to the Cβ region. The reaction mixture is then precipitated with ethanol and resuspended in 60 µl of H$_2$O.

II—Cloning and sequencing of cDNAs

⅓ of the product of the second amplification is digested with Sac II, separated on 1% agarose gel and purified by absorption on glass beads. The material is inserted in the Bluescript SK$^+$ vector (Stratagene, La Jolla, U.S.A.) and the recombinants obtained are used to transform the XL1-blue strains of E. Coli (Stratagene). After sedimentation in the presence of X-gal and IPTG, a test is carried out on the white colonies using a "dot blot" technique and a third oligonucleotide specific to the Cβ region (5'-TCTGCTTCTGATGGCTCAA) (SEQ ID No. 24) labelled with $^{32}$P is used as a probe. The plasmid DNA of positive colonies is extracted and sequencing takes place under the two strands by the process of termination of the dideoxy chain (Sanger et al. (16)) with Sequenase 2.0 (United States Biochemicals, Cleveland, U.S.A.) following the supplier's recommendations.

The sequences obtained were compared with published Vβ sequences using the method developed by Lipman and Pearson (17). The presumed start codons were identified by searching for the presence of the Kozak consensus sequence for the initiation sites of translations in the eukaryotic cells (Kozak (18)). The presence of hydrophobic leader sequences of the N-terminal side was detected by analysis of the hydrophobicity according to the method described by Kyte (19).

III—Southern blot analysis

The DNA was extracted from the human erythroleukaemic cell line K562 and digested with one of the following restriction enzymes: Eco RI, BamH I or Hind III. The DNA (15 micrograms) was subjected to electrophoresis on 0.7% agarose and transferred onto Nylon membranes as described by Triebel et al. (20). The hybridizations were carried out at 65° C. with 6×SSC, 0.5% of SDS, 5×Denhardt's and 100 micrograms of denatured salmon sperm DNA for 16 hours. The membranes were washed at 65° C. with 2×SSC, 0.2% of SDS.

As Vβ specific probes, are used the probes obtained by amplification of V-J-C cDNA using as a primer the poly-C primer and the C primer. The probes were purified on 1% agarose gel. DNA probes labelled with $^{32}$P were prepared from fragments purified on agarose by the Feinberg method (21).

IV—Results

By using the A-PCR method, 350 cDNA which hybridize with the Cβ clone were cloned, then sequenced. Among these, 226 cDNA correspond to the V-J-Cβ variable regions only.

The Vβ sequences of the invention are shown in the list of sequences under SEQ ID No. 2 to 19. The sequences SEQ ID No. 3 to 5 correspond to three new sub-families while the sequences SEQ ID No. 2 and 6 to 19 correspond to new members of Vβ sub-families or to extensions of known Vβ segments.

Vβw21 sub-family (SEQ ID No. 2)

This sub-family has been identified by the clone IGR b02 (SEQ ID No. 2).

This sequence shows for the coding part a similarity of about 85% with the sequence HSTCRB23 (Wilson et al. (41)).

Vβw22 sub-family (SEQ ID No. 3)

The segment SEQ ID No.3 has been defined as a consensus sequence from 23 distinct clones of cDNA. A C instead of a T is observed in position 322 and an A instead of a G is observed in position 350.

Vβw23 sub-family (SEQ ID No. 4)

The segment ID No. 4 has been defined as a consensus sequence from 4 distinct clones. A G instead of an A is observed in position 154 and an A instead of a G is observed in position 160. It shows a similarity of 75.7% with the sequence VB12A1 (Leiden already quoted) but shows a similarity of less than 75% with the other members of the Vβ5 sub-family (represented in FIG. 1). Therefore it is not part of the V 5 sub-family.

Vβw24 subfamily (SEQ ID No.5)

The segment SEQ ID No. 5 has been defined from 2 distinct clones of cDNA.

The Southern blot analyses of germinal line DNA subjected to digestion by endonucleases, using V-J-Cβ probes containing Vβ fragments corresponding to the Vβw21 to Vβw24 sub-families were carried out in "low stringency" hybridization conditions to identify the number of Vβ genetic segments belonging to each family and to characterize the DNA restriction fragments carrying these Vβ genetic segments. The representative results are shown in FIG. 7.

These analyses are compatible with the presence in the K 562 erythroleucemic cells of at least three genetic segments for the Vβw21 sub-family, two for the Vβw23 sub-family and one for the Vβw22 and Vβw24 sub-families.

The sizes of the germinal DNA restriction fragments are as follows:

Vβw21: EcoR I 1.7-,3- and 6.5 kb, Hind III 2.5-, 7.2-, 11.7-, 14- and 18 kb, BamH I 5.5-, 16.5- and 23 kb;

Vβw22: EcoR I 2.8 kb, Hind III 8.8 kb, BamH I 5.3 kb;

Vβw23: EcoR I 3.2- and 4.4 kb, Hind III 7.4-, 15.5- and 16.5 kb, BamH I 2.5- and 5.7 kb;

Vβw24: EcoR I 8 kb, Hind III 20 kb and 7.3 kb, BamH I 11- and 22 kb.

Vβ5 sub-family (FIG. 1):

SEQ ID No. 6 and 7 (IGR b06 and IGR b07)

These sequences show a similarity of 79 to 86% and 76 to 70% respectively with the 4 previously known segments VB12A1 (Leiden already quoted), HBP51 (Kimura (23)), PH24 (Tillinghast already quoted) and PL25 (Concannon (24)) and represent new members.

SEQ ID No. 8 and 9 (IGR b08 and IGR b09)

These sequences correspond to extensions of the 5' side of VB12A1 and PL25 clones respectively. For SEQ ID No. 8 two nucleotide substitutions are observed relative to VB12A1.

Figure 2:
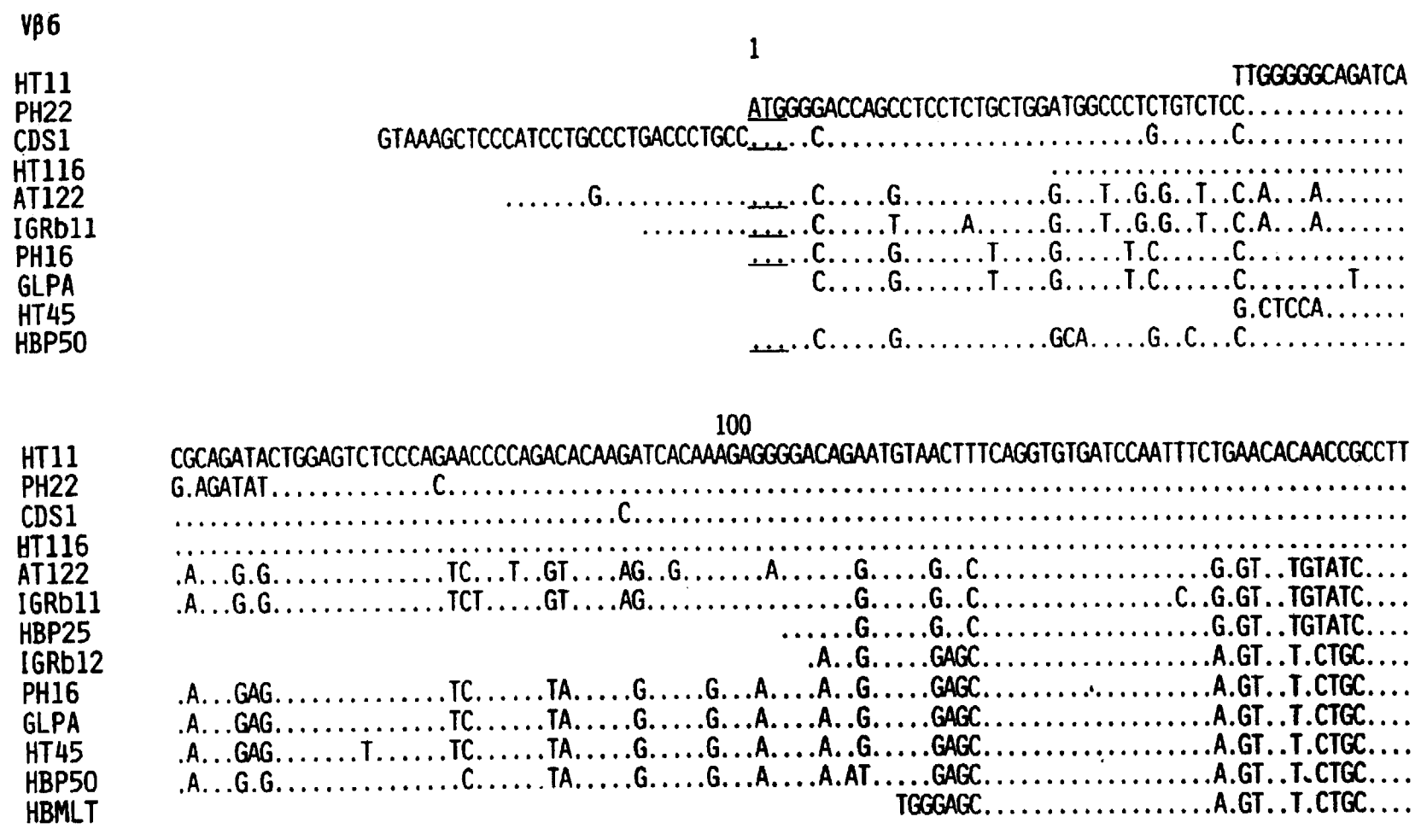
Figure 2A:
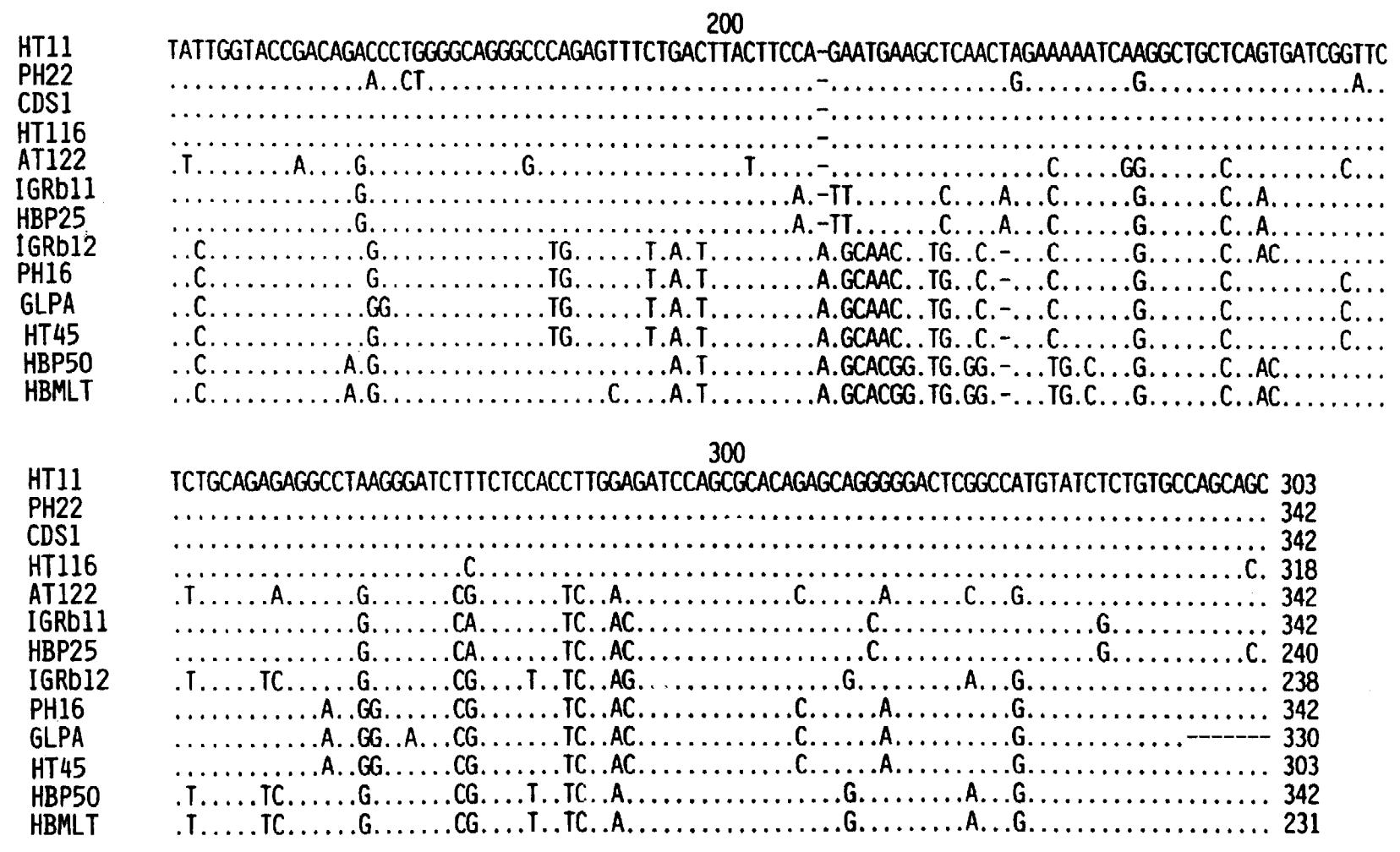

Vβ6 sub-family (FIGS. 2A and 2B):

SEQ ID No. 10 (IGR b11)

This sequence corresponds to an extension of the 5' side of clone HBP25 (Kimura, already quoted).

SEQ ID No. 11 (IGR b12)

This sequence which represents a new member shows a similarity of nucleotides of 94% with PH 16 (Tillinghast already quoted), GPPA (Li, already quoted) and HT45 (Kimura (25)).

Vβ12 sub-family (FIG. 3):

SEQ ID No. 12 (IGR b13)

This sequence which represents a new member shows a similarity of greater than 85% with the sequences PH27 (Tillinghast already quoted), and PL42 (Concannon, already quoted).

Vβ13 sub-family (FIG. 4):

SEQ ID No. 13, 14 and 15 (IGR b14, IGR b15 and IGR b16)

The sequences SEQ ID No. 13 and 14 which represent new members show a similarity of 78 to 91% and 77 to 79% respectively with the other known sequences HBVP34 (Kimura (23)) and CEM (Duby (26)).

The sequence SEQ ID No. 15 show a similarity of 94% with HBVP34. It should be noted that the sequence SEQ ID No. 15 shows an intron (represented by lower case characters) in the leader region. The sequence SEQ ID No. 15 is a consensus sequence. A C instead of a T is observed in position 231 and an A instead of a G is observed in position 259.

Vβ7 sub-family (FIG. 5):

SEQ ID No. 16 and 17 (IGR b17 and IGR b18)

These sequences show a strong similarity with the truncated sequence PL4.19 (Concannon, already quoted) and the extension of the 5' side up to the start signal of the translation.

SEQ ID NO. 18 (IGR b19)

This sequence extends the sequence PL4.9 (Concannon already quoted) of the 5' side up to the start signal of the translation.

Vβ9 sub-family (FIG. 6):

SEQ ID No. 19 (IGR b20)

This sequence extends the sequence PL2.6 (Concannon, already quoted) of the 5' side. A difference between the two sequences is observed in positions 98 and 100 corresponding to different amino acids.

The present invention also aims at providing specific oligonucleotides of different Vβ sub-families, which can be used as primers for the amplification of DNA corresponding to these different Vβ sub-families, with a view, for example, of a study of the expression of certain Vβ sub-families in a patient and finally of a diagnosis of immune disorders, as indicated above.

The predominant expression of certain Vβ sub-families has already been studied using an incomplete range of oligonucleotides.

In this way Sottini et al. (33) have shown, using a range of oligonucleotides, a predominant expression of certain Vβ's in patients suffering from rheumatoid arthritis.

Similarly, Choi Y. et al. (32) have shown, using a range of oligonucleotides, the stimulation of T lymphocytes by *Staphylococcus aureus* toxins by the intermediary of specific Vβ's.

The present invention aims to provide a complete range of oligonucleotides allowing the study, of both known Vβ sub-families and new Vβ sub-families of the invention and which are completely specific to each sub-family. Thus the oligonucleotides have been chosen and synthesized to this end and to the requirements of modifications of one or two nucleotides which have been introduced relative to the natural sequences to reduce the cross-reactions between sub-families.

Thus a subject of the present invention is also oligonucleotides which can be used as primers for the amplification of DNA corresponding to the variable regions of chains of T-cell receptors, chosen form the sequences SEQ ID No. 25 to 48.

Also a subject of the present invention is the use, as primers for the amplification of DNA corresponding to the variable regions of chains of T-cell receptors, of oligonucleotides chosen from the sequences SEQ ID No. 25 to 48.

Also a subject of the present invention is a detection process of nucleotides sequences coding for the V segments of T receptors or of cDNA corresponding to transcription products of the latter, in a biological sample, characterized in that it includes:

a) the amplification of DNA with at least one pair of primers formed by one of the oligonucleotides defined above and one oligonucleotide belonging to a Cβ segment, and b) the detection of amplified sequences with a Cβ probe.

The oligonucleotide belonging to a Cβ segment used for the amplification can be, in particular, chosen from the sequences SEQ ID No. 49 and 50.

To check the efficiency of the amplification, the operation is preferably carried out in the presence of a pair of control primers and the corresponding control sequence amplified using a corresponding control probe is detected.

This pair of control primers can correspond to two Cβ segments, for example the CαE and CαJ primers corresponding to sequences SEQ ID No. 55 and 56. A Cα detection probe (corresponding for example to the sequence SEQ ID NO. 57) is then used. But this pair of primers is advantageously constituted by two primers belonging to β-actin, notably those corresponding to sequences SEQ ID No. 52 and 53. Then a detection probe corresponding to a sequence of β-actin, such as the sequence SEQ ID No. 54, is used.

Also a subject of the present invention is a diagnostic kit for the implementation of the process defined previously, which includes:

a) at least one oligonucleotide chosen from the sequences SEQ ID No. 25 to 48, b) a Cβ primer, c) a Cβ probe.

In addition such a kit advantageously contains:

d) a pair of control primers, e) a control probe.

This kit can contain in particular:

a) the group of 24 oligonucleotides corresponding to sequences SEQ ID No. 25 to 48, b) a Cβ primer chosen from the sequences corresponding to sequences SEQ ID No. 49 and 50, c) a pair of control primers for β-actin having a sequence corresponding to sequences SEQ ID NO. 52 and 53 respectively, d) a Cβ probe corresponding to the sequence SEQ ID No. 51, e) a control probe for β-actin corresponding to the sequence SEQ ID No. 54.

In the information given in the list of sequences for the sequences 25 to 54, the sequences SEQ ID No. 25 to 45 correspond to sequences belonging to clones of known Vβ1 to Vβ20 sub-families (available from the EMBL database) or to sequences which differ from them by one or two nucleotides. The sequences SEQ ID No. 45, 46, 47 and 48 correspond to sequences belonging to clones of new sub-families of the invention, corresponding to sub-families provisionally designated Vβw21, Vβw22, Vβw23 and Vβw24 (w indicating that the designation is pending definitive designation).

The sequences SEQ ID No. 49 and 50 are two examples of Cβ oligonucleotides which can be used as primers for amplification.

The sequence SEQ ID No. 51 is the sequence of a Cβ probe which can be used for the detection of amplified DNAs.

Finally, the sequences SEQ ID No. 52, 53 and 54 are respectively the sequences of a pair of oligonucleotides belonging to the sequence of β-actin which can be used to check the amplification and the sequence of a probe for detecting the corresponding amplified DNAs.

In the list of sequences the position indicated is the position of the 5' end counting from the predicted initiation site of the ATG translation. In the case where the sequences are incomplete (unknown 5' region), the position (marked with an asterisk) is given relative to the first nucleotide of the sequence. The underlined nucleotides correspond to mismatches introduced relative to the natural sequence.

The oligonucleotides were sythesized with an Applied Biosystems 381 A automated DNA synthesizer using the β-cyano-ethylphosphoramidite method (Sinha N. et al. (34)) and following the protocol recommended by the manufacturer. The oligonucleotides were detritylated in the apparatus, cleaved form the support and deprotected with ammonia (at 60° C. for 5 hours). The crude products were purified by inverted phase high pressure chromatography on a μ-bondapak C18 column using an acetonitrile gradient (9 to 15%) in a 0.01M triethylammonum acetate buffer at pH 5.5.

The amplification carried out using the primers according to the invention can be, in particular, the technique of amplification by PCR (Polymerase Chain Reaction) as described by Saiki et al. (14) and in U.S. Pat. Nos. 4,683,195, 4,683,202, 4,889,818.

For the PCR, a double strand DNA can be used which is denatured or a cDNA obtained from RNA using reverse transcriptase as mentioned above.

The polymerization agent is a DNA polymerase, in particular, Taq polymerase.

Generally the amplification cycle is repeated 25 to 40 times.

The probes which are used for detecting the amplified sequences can be obtained by labelling the oligonucleotides with a radio-active isotope, which leads to detection by autoradiography, or by conjugation with an enzyme such as peroxidase (ECL Amersham system), alkaline phosphatase or β-galactosidase (Tropix Ozyme system), which leads to detection by chemiluminescence.

The following example illustrates the implementation of the detection process according to the invention.

The peripheral lymphocytes of a healthy individual were prepared by density gradient centrifugation. The total DNA was extracted according to a one-stage method by extraction with guanidium isothiocyanate, phenol and chloroform (Chomczynski, 13). The complementary DNA was synthesized in a final volume of 20 μl at 42° C. for one hour using 1 to 5 μg of total RNA, the reverse transcriptase and the CβB primer (1.25 uM).

The material obtained was then heated at 95° C. for 3 minutes before being subjected to an amplification according to the PCR technique using in parallel each of the specific Vβ primers corresponding to sequences SEQ ID No. 25 to 48 and the CβB primer specific to the Cβ region (SEQ ID No. 50). This amplification was carried out in a final volume of 10 µl per tube containing 50 mM of KCl, 10 mM of tris-HCl pH 8.3, 1.5 mM of MgCl$_2$, 0.1% (weight/volume) of gelatine, 200 µM of dNTP, 0.25 units of Taq polymerase and 0.25 µM of each primer. A control amplification was carried out in each tube from 25 mN of a DNA fragment of β-actin of 877 base pairs prepared by PCR and Act 1 and Act 2 primers (SEQ ID No. 52 and 53) specific to actin. 30 amplification cycles were carried out followed by a final elongation stage of 5 minutes at 72° C. Each cycle included a denaturation stage at 94° C. for one minute, a hybridization stage at 65° C. for one minute and an elongation period at 72° C. for one minute.

The products obtained were separated by electrophoresis on 2% agarose gel, transferred onto nylon membranes in an alkaline buffer and hybridized simultaneously with the CβC oligonucleotide probes (SEQ ID No. 51) and Act 3 (SEQ ID No. 54) labelled with $^{32}$P by the polynucleotidyl T4 kinase enzyme. The hybridization was carried out at 42° C. for 16 hours in a buffer containing 6×SSC, 0.5% SDS, 5×Denhardt's, 0.05% NaH$_2$PO$_4$ and 100 µg/ml of denatured salmon sperm DNA. The membranes were then washed with SSC 6×, 20 mM NaH$_2$PO$_4$, twice at ambient temperature for 5 minutes and once at 50° C. for 30 minutes then autoradiographed.

The results obtained are shown in FIG. 8.

The actin control (band of 877 base pairs) allows the amplification to be verified in all wells. A specific signal appears below this band the size of which corresponds to the size of corresponding amplified fragments, each fragment having a length corresponding to the distance between the locus of the specific Vβ oligonucleotide and the Cβ primer.

With the individual tested, FIG. 8 shows the preferential expression of certain genetic segments defined relative to the others. For example, the Vβ1 and 2 sub-families are more represented than the other sub-families.

Example of the preparation of anti V 13 monoclonal antibodies: RO-73 and JU-74 monoclonal antibodies 1) Immunizing cells The clone T 3025 (Moebius et al. (35)) was cultivated in complete medium containing DMEM (Seromed), 8% AB human serum, IL-2 and TCGF as described by Hercend et al. (36). Periodic restimulations were carried out on allogenic cells in the presence of IL-2. The messenger RNAs coding for the T receptor expressed by these cells were sequenced using the A-PCR technique and represent rearrangements of genetic segments Vα10 (sequence HAP58, Yoshikai et al. (37)) and Vβ13 (sequence IGRb16=SEQ ID No. 15 indicated above).

2) Immunization of mice 6-week old Biozzi mice (Curie Institute, Paris, France) were immunized with whole T cells of clone 3025. After a first intraperitoneal injection of 5×10$^6$ cells in Freund's complete adjuvant, the mice received three intraperitoneal injections of 5×10$^6$ cells in Freund's incomplete adjuvant at three-week intervals. Two weeks after the last intraperitoneal injection the mice received an intravenous injection of 2×10$^6$ viable cells. The mice were killed three days later and the spleen was removed.

3) Fusion

The fusion of spleen cells with the myeloma which does not secrete NS-1 was carried out according to the Kohler and Milstein method (38). The NS-1 cells (Kohler and Milstein (39)) were cultivated in a medium containing DMEM (Seromed), 8-azaguanine (Sigma, Saint Louis, Mich.), 10% horse serum (Seromed, lot No. 5Z04), penicillin and streptomycin (Eurobio), glutamine (Seromed, 200 mM) and sodium pyruvate (Gibco, 100 mM).

The splenocytes were fused with NS-1 cells with polyethylene-glycol (PEG 1000, Merck) in a ratio of 4 spleen cells per one myeloma cell. After the fusion, the cells were cultivated at 3×10$^6$ cells per ml in plates of 96 wells (Nunc) in a HAT selection medium containing DMEM, 10% horse serum, 10% foetal calf serum (Seromed, lot No. 219195), aminopterin (Gibco), hypoxanthine and thymidine (Gibco), penicillin and streptomycin, glutamine, sodium pyruvate and NCTC 109 (Eurobio). Fresh medium was added to the wells 2 days (50 µl per well) and 9 days (100 µl per well) after fusion. The culture was carried out at 37° C., in an incubator containing 10% CO$_2$.

4) Screening of hybridomas

The supernatant of hybridomas obtained was collected 15 days after fusion and its reactivity was tested with the immunizing cell by indirect immunofluorescence and analysed by flow cytometry analysis. In brief, the T3025 cells were incubated at 4° C. for 30 minutes with the hybridoma supernatant (100 µl per 300,000 cells), washed and labelled with a mouse anti-immunoglobulin goat antibody conjugated with fluorescein (Coulter Electronics, Hialeah, Fla.). The cells were then analyzed by flow cytometry analysis. (Coulter Profile). As is shown in FIGS. 9A and 10A, the supernatants of hybridomas RO-73 and JU-74 allow the labelling of 100% of the cells of immunizing clone 3025. An anti-CD3 antibody (OKT3 Ortho-Co) and the anti-clonotype NKTa antibody (IgG1, Hercend et al (40)) served respectively as positive and negative controls in this experiment.

5) Anti-T receptor specificity

The anti-T receptor specificity of the monoclonal antibodies was analyzed according to the following criteria:

1—the antibodies must recognize the immunizing T clone 3025 but not a T clone carrying a different T-cell receptor (TCR), for example the clone 12410 (Moebius et al., (35)) expressed TCR: Vα3/Vβ17).

2—The antibodies must react with a low percentage of circulating lymphocytes (PBL).

3—The structure of the surface recognized by the antibodies on the immunizing cell must co-modulate with the CD3 molecule at the time of the incubation of the cells in the presence of anti-CD3 antibodies (Meuer et al. (1)).

As FIGS. 9 and 10 show, the supernatants of hybridomas RO-73 and JU-74 react with 100% of the cells of immunising clone 3025 (FIGS. 9A and 10A), less than 2% of the cells of clone 12410 (FIGS. 9B and 10A) and 1 to 3% of the PBLs (FIGS. 9C and 10C).

For the co-modulation experiments, the cells of clone 3025 (10$^6$ cells per ml) were incubated in medium only or in the presence of anti-CD3 antibodies (OKT3) in 24-well culture plates. After incubation for 24 hours the cells were collected and labelled with the supernatant of hybridoma RO-73 or JU-74, anti-CD3 monoclonal antibody or an anti-CD2 control monoclonal antibody (Coultronics Co.) then analyzed by flow cytometry analysis. As FIGS. 11 and 12 show, the flow cytometry analysis of cells incubated in the presence of anti-CD3 monoclonal antibody (FIGS. 11B and 12B) shows a diminution of the fluorescence intensity for the anti-CD3 monoclonal antibody as well as for RO-73 and JU-74, while the labelling intensity with anti-CD2 monoclonal antibody increases in comparison to the intensity obtained respectively in the absence of anti-CD3 antibody (FIG. 11A and FIG. 11B). These results indicate that the molecule recognized by the RO-73 and JU-74 antibodies co-modulates with the CD3 molecule at the surface of the cells of clone T 3025.

6) Isolation of a sub-clone

The cells of the initial hybridomas, respectively RO-73 and JU-74 were distributed on culture plates at the rate of 0.5 cell per well in complete HAT medium, on irradiated syngenic spleen cells. Three sub-clones were selected for each of the hybridomas RO-73 and JU-74. These cells produce monoclonal antibodies whose reactivity is identical to that of the initial hybridomas (results not shown).

The sub-clones were cultivated in non-selective medium containing DMEM, 10% foetal calf serum, 10% horse serum, hypoxanthine, thymidine, penicillin and streptomycin, glutamine, sodium pyruvate and NCTC 109.

The cells of the hybridomas or sub-clones were frozen in foetal calf serum containing 10% of dimethyl sulphoxide (DMSO, Merck) and stored in liquid nitrogen.

7) Isotyping of monoclonal antibodies

The isotypes were determined by immunodiffusion on a solid support using an "INNO-LIA mouse mAb isotyping" kit (Innogenetics) for the determination of the isotypes of immunoglobulins in the supernatants of the culture. RO-73 and JU-74 are mouse immunoglobulins of isotype IgG1, kappa.

8) Purification of monoclonal antibodies

Ascites were produced in nude mice. The ascitic liquid obtained was filtered through cotton to eliminate the fibrin and precipitated with sodium sulphate (18%). The deposit obtained was suspended in PBS buffer, ⅓ diluted in a buffer (NaCl 4.5M, Glycine 2.25M, pH 8.8) and loaded into a column of Protein A-Sepharose 4 Fast Flow equilibrated in the loading buffer (NaCl 3M, glycine 1.5M, pH 8.8). A major peak of immunoglobulins was eluted at pH 6 using successive elution buffers of decreasing pH. This major peak was purified on an ion exchange column (Q Sepharose Fast Flow) in a Tris 50 mM, pH 8 buffer and eluted with an NaCl gradient.

The purity of the preparation was verified by electrophoresis in a PHAST system (Pharmacia LKB, Uppsala, Sweden) and the purified immunoglobulins were tested by indirect immuno-fluorescence on the cell 3025, as indicated previously.

As an example, for 30 ml of ascite of the hybridoma RO-73, 32 mg of purified immunoglobulins was obtained after purification on Protein A and Q Sepharose Fast Flow.

9) Percentage of PBL recognized by the monoclonal antibodies

The percentage of circulating lymphocytes recognized respectively by the monoclonal antibodies RO-73 and JU-74 was determined for 10 different healthy donors. The results are shown in Table 1. The monoclonal antibody JU-74 recognizes less than 0.5% to 2.1% of the PBLs (average 1.08%) and the monoclonal antibody RO-73 recognizes from 0.5% to 2.2% of the PBLs according to the individuals (average 1.09%). For a given individual, the monoclonal antibodies RO-73 and JU-74 recognize respectively approximately the same percentages of circulating lymphocytes.

TABLE 1

Reactivity of monoclonal antibodies RO-73 and JU-74 with peripheral blood cells

| Donor | RO-73 | JU-74 |
|---|---|---|
| BQ | 2,2 | 2,1 |
| BY | 0,9 | 1,1 |
| BZ | <0,5 | <0,5 |
| CA | 0,5 | <0,5 |
| CB | 0,5 | 0,6 |
| CD | 1,8 | 1,7 |
| CE | 0,4 | 0,3 |
| CH | 1,6 | 1,3 |
| CI | 1,4 | 1,2 |
| CJ | 1,1 | 1,5 |

10) Purification of PBLs recognized by the monoclonal antibodies

The PBLs recognized respectively by the monoclonal antibodies RO-73 and JU-74 were purified from a normal donor using a positive selection process with magnetic beads (Dynabeads, Dynal). In brief, 1 to $4 \times 10^9$ PBL were labelled by one or other of the above purified monoclonal antibodies and incubated with ready-to-use Dynabeads M-450 beads covered with a mouse anti-IgG goat serum, in the proportion of 3 beads per labelled cell. The positive cells were then separated using a magnet. After several washings, the cells were incubated with an excess of mouse anti-IgG goat immunoglobulins ("Detach-a-beads", Dynatech) in order to detach the magnetic beads then directly analyzed by flux cytometry analysis after labelling with the monoclonal antibody RO-73 or the monoclonal antibody JU-74, respectively.

The selected positive cells were cultivated in a microplate in the presence of IL-2 on the irradiated allogenic cells then purified again with magnetic beads after culturing for about a week in order to obtain a preparation with a purity greater than 95%.

For the monoclonal antibody JU-74, $8 \times 10^6$ positive cells of 96% purity were obtained, after a one-week culture, from $1 \times 10^9$ PBL from a healthy donor containing initially 1.7% of JU-74+ cells.

For the monoclonal antibody RO-73, $9 \times 10^6$ positive cells of 98% purity were obtained, after a 10-day culture, from $1.2 \times 10^9$ PBL from a healthy donor containing initially 2.4% of RO-73+ cells.

From the purified RO-73+ and JU-74+ cells selected in this way, the respective cell lines were established; each line is 100% recognized by the two monoclonal antibodies, which shows that the two monoclonal antibodies recognize the same cells in peripheral blood.

Analysis of TCR transcripts expressed in the PBLs recognized by RO-73 and JU-74 by PCR techniques a) Method of analysing the β transcripts The range of specific oligonucleotides of Vβ segments of type Vβ1 to Vβ24 described above (SEQ ID No. 25 to No. 48) were used as specific primers for analysing the TCRβ transcripts expressed in the RO-73+ and JU-74+ cells. The procedure used is identical to that described in the example above for the peripheral lymphocytes of a healthy individual. In brief, after preparation of the RNA according to the Chomczynski method (13), the complementary DNA was synthesized using reverse transcriptase and the CβB primer (SEQ ID No. 50). The material obtained was subjected to 30 amplification cycles according to the PCR technique using in parallel each of the specific Vβ primers corresponding to the sequences SEQ ID No. 25 to 48 and the specific CβB primer of the Cβ region (SEQ ID No. 50) as described previously.

The amplified products obtained were separated by electrophoresis on 2% agarose gel, transferred onto nylon membranes and hybridized with the CβC oligonucleotide probe (SEQ ID No. 51) labelled with $^{32}$P. The membranes were then washed as described above then autoradiographed.

The sequencing of the transcripts of the TCRβ chain was carried out following the cloning and sequencing method described previously for the cDNA. For example, the material amplified by the specific oligonucleotide of the Vβ13 sub-family (SEQ ID No. 37) was digested by the enzyme SacII and purified by electrophoresis on agarose gel. The material obtained was introduced into the pBS SK$^+$ vector (as described above for the A-PCR technique) and used to transfect the E. Coli XL-1 blue bacteria. The transformed colonies obtained were tested by dot-blot hybridization using the CβC oligonucleotide probe (SEQ ID NO. 51) labelled with $^{32}$P. The plasmid DNA was sequenced as described previously.

b) Method of analysing the α transcripts

A methodology resembling that described for the β transcripts was applied to the analysis of the transcripts of the TCRα chain using as specific primers a range of specific oligonucleotides of Vα segments of the Vα1 to Vα29 type and specific oligonucleotides of the constant Cα region (CαB oligonucleotide for the synthesis of the complementary DNA and the amplification by PCR and CαC oligonucleotide for the detection probe). The sequences of these oligonucleotides are indicated in Table 2.

monoclonal antibody RO-73. It should be noted that numerous different Vα segments are expressed in these cells (FIG. 13A). On the other hand, only the specific oligonucleotide of the sequences of the Vβ13 sub-family allows an amplification of the cDNA (FIG. 13B).

Identical results were obtained for the TCRβ transcripts expressed in the JU-74+ cells recognized by the monoclonal antibody JU-74 (results not shown).

In addition, the β transcripts which correspond to the Vβ13 sub-family expressed by the JU-74+ cells were sequenced from cells previously isolated in order to determine, among the 5 known or new members of the Vβ13 sub-family (FIG. 4), those whose products are recognized by the monoclonal antibody JU-74. Table 3 shows the results obtained after analysis of these sequences. The eight different sequences of Vβ13 obtained all correspond to a rearrangement of the new Vβ13 genetic segment IGRb16 (SEQ ID No. 15) with different J segments and N regions.

TABLE 3

| | Expression of the transcripts of the β chain in JU-74+ cells | | | |
|---|---|---|---|---|
| cDNA clones | Vβ | member | Jβ | Region N |
| B001 | 13 | IGRb16I | J2.1 | ≠ |
| B002 | 13 | IGRb16I | J1.6 | ≠ |
| B006 | 13 | IGRb16I | J1.1 | ≠ |
| B007 | 13 | IGRb16I | J2.1 | ≠ |

TABLE 2

| Sequence | Type | |
|---|---|---|
| 5'-GGCATTAACGGTTTTGAGGCTGGA-3' | Vα1 | (SEQ ID NO:58) |
| 5'-CAGTGTTCCAGAGGGAGCCATTGC-3' | Vα2 | (SEQ ID NO:59) |
| 5'-CCGGGCAGCAGACACTGCTTCTTA-3' | Vα3 | (SEQ ID NO:60) |
| 5'-TTGGTATCGACAGCTTCCCTCCCA-3' | Vα4 | (SEQ ID NO:61) |
| 5'-CGGCCACCCTGACCTGCAACTATA-3' | Vα5 | (SEQ ID NO:62) |
| 5'-TCCGCCAACCTTGTCATCTCCGCT-3' | Vα6 | (SEQ ID NO:63) |
| 5'-GCAACATGCTGGCGGAGCACCCAC-3' | Vα7 | (SEQ ID NO:64) |
| 5'-CATTCGTTCAAATGTGGGCAAAAG-3' | Vα8 | (SEQ ID NO:65) |
| 5'-CCAGTACTCCAGACAACGCCTGCA-3' | Vα9 | (SEQ ID NO:66) |
| 5'-CACTGCGGCCCAGCCTGGTGATAC-3' | Vα10 | (SEQ ID NO:67) |
| 5'-CGCTGCTCATCCTCCAGGTGCGGG-3' | Vα11 | (SEQ ID NO:68) |
| 5'-TCGTCGGAACTCTTTTGATGAGCA-3' | Vα12 | (SEQ ID NO:69) |
| 5'-TTCATCAAAACCCTTGGGGACAGC-3' | Vα13 | (SEQ ID NO:70) |
| 5'-CCCAGCAGGCAGATGATTCTCGTT-3' | Vα14 | (SEQ ID NO:71) |
| 5'-TTGCAGACACCGAGACTGGGGACT-3' | Vα15 | (SEQ ID NO:72) |
| 5'-TCAACGTTGCTGAAGGGAATCCTC-3' | Vα16 | (SEQ ID NO:73) |
| 5'-TGGGAAAGGCCGTGCATTATTGAT-3' | Vα17 | (SEQ ID NO:74) |
| 5'-CAGCACCAATTTCACCTGCAGCTT-3' | Vα18 | (SEQ ID NO:75) |
| 5'-ACACTGGCTGCAACAGCATCCAGG-3' | Vα19 | (SEQ ID NO:76) |
| 5'-TCCCTGTTTATCCCTGCCGACAGA-3' | Vα20 | (SEQ ID NO:77) |
| 5'-AGCAAAATTCACCATCCCTGAGCG-3' | Vα21 | (SEQ ID NO:78) |
| 5'-CCTGAAAGCCACGAAGGCTGATGA-3' | Vα22 | (SEQ ID NO:79) |
| 5'-TGCCTCGCTGGATAAATCATCAGG-3' | Vαw23 | (SEQ ID NO:80) |
| 5'-CTGGATGCAGACACAAAGCAGAGC-3' | Vαw24 | (SEQ ID NO:81) |
| 5'-TGGCTACGGTACAAGCCGGACCCT-3' | Vαw25 | (SEQ ID NO:82) |
| 5'-AGCGCAGCCATGCAGGCATGTACC-3' | Vαw26 | (SEQ ID NO:83) |
| 5'-AAGCCCGTCTCAGCACCCTCCACA-3' | Vαw27 | (SEQ ID NO:84) |
| 5'-TGGTTGTGCACGAGCGAGACACTG-3' | Vαw28 | (SEQ ID NO:85) |
| 5'-GAAGGGTGGAGAACAGATGCGTCG-3' | Vαw29 | (SEQ ID NO:86) |
| 5'-ATACACATCAGAATTCTTACTTTG-3' | CαA | (SEQ ID NO:87) |
| 5'-GTTGCTCCAGGCCGCGGCACTGTT-3' | CαB | (SEQ ID NO:88) |
| 5'-GTCACTGGATTTAGAGTCT-3' | CαC | (SEQ ID NO:57) | c) Results

FIG. 13 shows the results obtained for the analysis of transcripts of TCRα chains (FIG. 13A) and β chains (FIG. 13B) expressed by the RO-73+ cells recognized by the

TABLE 3-continued

| | Expression of the transcripts of the β chain in JU-74+ cells | | | |
|---|---|---|---|---|
| cDNA clones | Vβ | member | Jβ | Region N |
| B009 | 13 | IGRb16I | J1.6 | ≠ |
| B010 | 13 | IGRb16I | J2.6 | ≠ |
| B011 | 13 | IGRb16I | J1.3 | ≠ |
| B012 | 13 | IGRb16I | J1.2 | ≠ |

All these results show that the monoclonal antibodies RO-73 and JU-74 are specific to products of genetic segments belonging to the Vβ13 sub-family.

More precisely, the monoclonal antibodies JU-74 and RO-73 have the same specificity and recognize exclusively the product of the new Vβ13 genetic segment IGRb16 of the invention. (SEQ ID No. 15 indicated above).

The following hybridoma cell lines were deposited with the Collection Nationale de Culture de Microorganismes (CNCM—Pasteur Institute): JU-74 and RO-73 on the 12th Feb. 1992 under the numbers I-1173 and I-1172.

REFERENCES

1. Meuer, S. C., et al., J. Exp. Med. 1983. 157:705.
Moingeon, P., et al., Nature 1986a. 323:638.
3. Brenner, M. B., et al., Nature 1986. 322:145.
4. Bank, I., et al., Nature 1986. 322:179.
5. Davis, M. M., et al., Nature 1988. 334:395.
6. Crews, S., et al., Cell 1981. 25:59.
7. Wilson, R. K., et al., Immunological Reviews 1988c. 101:149.
8. Robinson, M. A., Proc. Natl. Acad. Sci. U.S.A. 1989. 86:9422.
9. Leiden, J. M., et al., Proc. Natl. Acad. Sci. U.S.A. 1986. 83:4456.
10. Reynolds 1986.
11. Li, Y., et al., J. Exp. Med. 1990. 171:221.
12. Chirgwin, J. M., et al. Biochemistry 1979. 18:5294.
13. Chomczynski, P., et al., Anal. Biochem. 1987. 162:136.
14. Saiki, R. K., et al., Science 1988. 239:487.
15. Loh, E. Y., et al., Science 1989. 243:217.
16. Sanger, F., et al., Proc. Natl. Acad. Sci. U.S.A. 1977. 74:5463.
17. Lipman, D. J., et al., Science 1985. 227:1435.
18. Kozak, M., Nucl. Acids Res. 1984. 12:857.
19. Kyte, J., et al., R. F., J. Mol. Biol. 1982. 157:105.
20. Triebel, F., et al., J. Immun. 1988. 140:300.
21. Feinberg, A. P., et al., Anal. Bichem. 1983. 132:6.
22. Tillinghast, J. P., et al., Science 1986. 248:879.
23. Kimura, N., et al., J. Exp. Med. 1986. 164:739.
24. Concannon, P., et al., Proc.
25. Kimura, N., et al., Eur. J. Immunol. 1987. 17:375.
26. Duby, A. D., et al., Proc. Natl. Acad. Sc. U.S.A. 1986. 83:4890.
27. Vardenbark, A., et al., Nature, 341, 541.
28. Janeway, C., Nature, 341, 482.
29. Lin, Y., J. Exp. Med., 171, 221.
30. Acha-Orbea, H., EMBO Journal, 1990, 9,12, 3815.
31. Kappler, J., Science 244, 811.
32. Choi, Y., PNAS, 86, 8941.
33. Sottini A. et al., Eur. J. Immunol., 1991, 21, 461.
34. Sinha N. et al., Nucleic Acids Res. 1984, 12, 4539.
35. Moebius, U. et al., Eur. J. Immunol. 1990, 20, 889.
36. Hercend, T. et al., Cellular Immunol., 1984, 86, 381.
37. Yoshikai, Y. et al. J. Exp. Med., 1986, 164, 90.
38. Kohler, G. and Milstein, C., Nature, 1975, 256, 495.
39. Kohler, G. and Milstein, C., Eur. J. Immunol., 1976, 511.
40. Hercend, T. et al., J. Exp. Med., 158, 1983, 1547.
41. Wilson, R. K. et al., Immunogenetics, 1990, 32, 406.

What is claimed is:

1. An isolated nucleic acid coding for a variable region of a β chain of an human T lymphocyte receptor, said nucleic acid having a nucleotide sequence chosen from any one of the nucleotide sequences of SEQ ID NOS: 2 to 6 and 8 to 19.

2. An isolated nucleic acid that is a fragment of a nucleic acid of claim 1 having any one of the nucleotide sequences of 1 to 195 of SEQ ID NO: 16,
1 to 99 of SEQ ID NO: 17,
1 to 113 of SEQ ID NO: 18 or
1 to 186 of SEQ ID NO: 19.

3. An isolated nucleic acid coding for a variable region of a β chain of an human T lymphocyte receptor, said nucleic acid having a nucleotide sequence chosen from any one of the nucleotide sequences of SEQ ID NOS: 2 to 5.

4. An isolated nucleic acid coding for a variable region of a β chain of an human T lymphocyte receptor, said nucleic acid having a nucleotide sequence chosen from any one of the nucleotide sequences of SEQ ID NOS: 6 and 8 to 15.

5. An isolated nucleic acid that is a fragment of a nucleic acid of claim 4 having any one of the nucleotide sequences of 1 to 155 of SEQ ID NO: 8,
1 to 125 of SEQ ID NO: 9 or
1 to 111 of SEQ ID NO: 10.

6. A peptide encoded by a nucleotide sequence selected from the group consisting of 46 to 387 of SEQ ID NO: 2,
54 to 395 of SEQ ID NO: 3,
18 to 329 of SEQ ID NO: 4,
28 to 366 of SEQ ID NO: 5,
2 to 238 of SEQ ID NO: 6,
72 to 410 of SEQ ID NO: 8,
42 to 380 of SEQ ID NO: 9,
10 to 351 of SEQ ID NO: 10,
2 to 238 of SEQ ID NO: 11,
1 to 294 of SEQ ID NO: 12,
31 to 369 of SEQ ID NO: 13,
18 to 356 of SEQ ID NO: 14,
58 to 345 of SEQ ID NO: 15,
112 to 450 of SEQ ID NO: 16,
16 to 354 of SEQ ID NO: 17,
30 to 368 of SEQ ID NO: 18, and
94 to 432 of SEQ ID NO: 19.

* * * * *

SEQUENCE LISTING ( 1 ) GENERAL INFORMATION:

( i i i ) NUMBER OF SEQUENCES: 87

( 2 ) INFORMATION FOR SEQ ID NO:2:

( i ) SEQUENCE CHARACTERISTICS:
        ( A ) LENGTH: 387
        ( B ) TYPE: NUCLEOTIDE
        ( C ) STRANDEDNESS: DOUBLE
        ( D ) TOPOLOGY: LINEAR ( i i ) MOLECULE TYPE: cDNA TO mRNA ( v i ) ORIGINAL SOURCE:
        ( A ) ORGANISM: HUMAN
        ( H ) CELL LINE: HUMAN T LYMPHOCYTE ( i x ) FEATURE:
        ( A ) NAME/KEY: IGR b 02
        ( D ) OTHER INFORMATION: V BETA w21

( x i ) SEQUENCE DESCRIPTION: SEQ ID NO:2:

```
AGTGACCCTG ATCTGGCAAA GCTTCCATCC TGCCCTGACC CTGCC ATG                    48
                                                   MET
                                                   1

GGT ACC AGG CTC CTC TGC CGG GTG GCC TTC TGT CTC CTG GTG GAA GAA         96
Gly Thr Arg Leu Leu Cys Arg Val Ala Phe Cys Leu Leu Val Glu Glu
        5                   10                  15
```

| | | | | | | | | | | | | | | | |
|---|---|---|---|---|---|---|---|---|---|---|---|---|---|---|---|
| CTC | ATA | GAA | GCT | GGA | GTG | GTT | CAG | TCT | CCC | AGA | TAT | AAG | ATT | ATA | GAG | 144 |
| Leu | Ile | Glu | Ala | Gly | Val | Val | Gln | Ser | Pro | Arg | Tyr | Lys | Ile | Ile | Glu | |
| | 20 | | | | | | 25 | | | | | 30 | | | | |
| AAA | AAG | CAG | CCT | GTG | GCT | TTT | TGG | TGC | AAT | CCT | ATT | TCT | GGC | CAC | AAT | 192 |
| Lys | Lys | Gln | Pro | Val | Ala | Phe | Trp | Cys | Asn | Pro | Ile | Ser | Gly | His | Asn | |
| 35 | | | | | 40 | | | | | | 45 | | | | | |
| ACC | CTT | TAC | TGG | TAC | CGG | CAG | AAC | TTG | GGA | CAG | GGC | CCG | GAG | CTT | CTG | 240 |
| Thr | Leu | Tyr | Trp | Tyr | Arg | Gln | Asn | Leu | Gly | Gln | Gly | Pro | Glu | Leu | Leu | |
| 50 | | | | | 55 | | | | | 60 | | | | | 65 | |
| ATT | CGA | TAT | GAG | AAT | GAG | GAA | GCA | GTA | GAC | GAT | TCA | CAG | TTG | CCT | AAG | 288 |
| Ile | Arg | Tyr | Glu | Asn | Glu | Glu | Ala | Val | Asp | Asp | Ser | Gln | Leu | Pro | Lys | |
| | | | | 70 | | | | | 75 | | | | | 80 | | |
| GAT | CGA | TTT | TCT | GCA | GAG | AGG | CTC | AAA | GGA | GTA | GAC | TCC | ACT | CTC | AAG | 336 |
| Asp | Arg | Phe | Ser | Ala | Glu | Arg | Leu | Lys | Gly | Val | Asp | Ser | Thr | Leu | Lys | |
| | | | | 85 | | | | | 90 | | | | | 95 | | |
| ATC | CAG | CCT | GCA | GAG | CTT | GGG | GAC | TCG | GCC | GTG | TAT | CTC | TGT | GCC | AGC | 384 |
| Ile | Gln | Pro | Ala | Glu | Leu | Gly | Asp | Ser | Ala | Val | Tyr | Leu | Cys | Ala | Ser | |
| | | 100 | | | | | 105 | | | | | 110 | | | | |
| AGC | | | | | | | | | | | | | | | | 387 |
| Ser | | | | | | | | | | | | | | | | |

( 2 ) INFORMATION FOR SEQ ID NO:3:

( i ) SEQUENCE CHARACTERISTICS:
     ( A ) LENGTH: 395
     ( B ) TYPE: NUCLEOTIDE
     ( C ) STRANDEDNESS: DOUBLE
     ( D ) TOPOLOGY: LINEAR ( i i ) MOLECULE TYPE: cDNA TO mRNA ( v i ) ORIGINAL SOURCE:
     ( A ) ORGANISM: HUMAN
     ( H ) CELL LINE: HUMAN T LYMPHOCYTE ( i x ) FEATURE:
     ( A ) NAME/KEY: IGR b 03
     ( D ) OTHER INFORMATION: V BETA w22

( x i ) SEQUENCE DESCRIPTION: SEQ ID NO:3:

| | | | | | | | | | | | | | | | |
|---|---|---|---|---|---|---|---|---|---|---|---|---|---|---|---|
| | | | ACAGGACCAG | ATGCCTGAGC | TAGGAAAGGC | CTCATTCCTG | CTGTGATC | | | | | | | | 48 |
| CTGCC | ATG | GAT | ACC | TGG | CTC | GTA | TGC | TGG | GCA | ATT | TTT | AGT | CTC | TTG | 95 |
| | Met | Asp | Thr | Trp | Leu | Val | Cys | Trp | Ala | Ile | Phe | Ser | Leu | Leu | |
| | 1 | | | 5 | | | | | 10 | | | | | | |
| AAA | GCA | GGA | CTC | ACA | GAA | CCT | GAA | GTC | ACC | CAG | ACT | CCC | AGC | CAT | CAG | 143 |
| Lys | Ala | Gly | Leu | Thr | Glu | Pro | Glu | Val | Thr | Gln | Thr | Pro | Ser | His | Gln | |
| 15 | | | | 20 | | | | | 25 | | | | | 30 | |
| GTC | ACA | CAG | ATG | GGA | CAG | GAA | GTG | ATC | TTG | CGC | TGT | GTC | CCC | ATC | TCT | 191 |
| Val | Thr | Gln | Met | Gly | Gln | Glu | Val | Ile | Leu | Arg | Cys | Val | Pro | Ile | Ser | |
| | | | | 35 | | | | 40 | | | | | 45 | | |
| AAT | CAC | TTA | TAC | TTC | TAT | TGG | TAC | AGA | CAA | ATC | TTG | GGG | CAG | AAA | GTC | 239 |
| Asn | His | Leu | Tyr | Phe | Tyr | Trp | Tyr | Arg | Gln | Ile | Leu | Gly | Gln | Lys | Val | |
| | | | 50 | | | | | 55 | | | | | 60 | | |
| GAG | TTT | CTG | GTT | TCC | TTT | TAT | AAT | AAT | GAA | ATC | TCA | GAG | AAG | TGT | GAA | 287 |
| Glu | Phe | Leu | Val | Ser | Phe | Tyr | Asn | Asn | Glu | Ile | Ser | Glu | Lys | Ser | Glu | |
| | | 65 | | | | | 70 | | | | | 75 | | | |
| ATA | TTC | GAT | GAT | CAA | TTC | TCA | GTT | GAA | AGG | CCT | GAT | GGA | TCA | AAT | TTC | 335 |
| Ile | Phe | Asp | Asp | Gln | Phe | Ser | Val | Glu | Arg | Pro | Asp | Gly | Ser | Asn | Phe | |
| | 80 | | | | | 85 | | | | | 90 | | | | |
| ACT | CTG | AAG | ATC | CGG | TCC | ACA | AAG | CTG | GAG | GAC | TCA | GCC | ATG | TAC | TTC | 383 |
| Thr | Leu | Lys | Ile | Arg | Ser | Thr | Lys | Leu | Glu | Asp | Ser | Ala | Met | Tyr | Phe | |
| 95 | | | | | 100 | | | | | 105 | | | | | 110 | |
| TGT | GCC | AGC | AGT | | | | | | | | | | | | | 395 |
| Cys | Ala | Ser | Ser | | | | | | | | | | | | | |

( 2 ) INFORMATION FOR SEQ ID NO:4:

( i ) SEQUENCE CHARACTERISTICS:
        ( A ) LENGTH: 329
        ( B ) TYPE: NUCLEOTIDE
        ( C ) STRANDEDNESS: DOUBLE
        ( D ) TOPOLOGY: LINEAR ( i i ) MOLECULE TYPE: cDNA TO mRNA ( v i ) ORIGINAL SOURCE:
        ( A ) ORGANISM: HUMAN
        ( H ) CELL LINE: HUMAN T LYMPHOCYTE ( i x ) FEATURE:
        ( A ) NAME/KEY: IGR b 04
        ( D ) OTHER INFORMATION: V BETA w23

( x i ) SEQUENCE DESCRIPTION: SEQ ID NO:4:

```
             AGCTCCTCTG  CCATGTC ATG CTT TGT CTC CTG GGA GCA GGT TCA GTG      47
                                 Met Leu Cys Leu Leu Gly Ala Gly Ser Val
                                  1           5                        10

GCT GCT GGA GTC ATC CAG TCC CCA AGA CAT CTG ATC AAA GAA AAG AGG            95
Ala Ala Gly Val Ile Gln Ser Pro Arg His Leu Ile Lys Glu Lys Arg
             15                  20                  25

GAA ACA GCC ACT CTG AAA TGC TAT CCT ATC CCT AGA CAC GAC ACT GTC           143
Glu Thr Ala Thr Leu Lys Cys Tyr Pro Ile Pro Arg His Asp Thr Val
             30                  35                  40

TAC TGG TAC CAG CAG GGT CCA GGT CAG GAC CCC CAG TTC CTC ATT TCG           191
Tyr Trp Tyr Gln Gln Gly Pro Gly Gln Asp Pro Gln Phe Leu Ile Ser
             45                  50                  55

TTT TAT GAA AAG ATG CAG AGC GAT AAA GGA AGC ATC CCT GAT CGA TTC           239
Phe Tyr Glu Lys Met Gln Ser Asp Lys Gly Ser Ile Pro Asp Arg Phe
         60                  65                  70

TCA GCT CAA CAG TTC AGT GAC TAT CAT TCT GAA CTG AAC ATG AGC TCC           287
Ser Ala Gln Gln Phe Ser Asp Tyr His Ser Glu Leu Asn Met Ser Ser
 75                  80                  85                  90

TTG GAG CTG GGG GAC TCA GCC CTG TAC TTC TGT GCC AGC AGC                   329
Leu Glu Leu Gly Asp Ser Ala Leu Tyr Phe Cys Ala Ser Ser
                 95                 100
```

( 2 ) INFORMATION FOR SEQ ID NO:5:

( i ) SEQUENCE CHARACTERISTICS:
        ( A ) LENGTH: 366
        ( B ) TYPE: NUCLEOTIDE
        ( C ) STRANDEDNESS: DOUBLE
        ( D ) TOPOLOGY: LINEAR ( i i ) MOLECULE TYPE: cDNA TO mRNA ( v i ) ORIGINAL SOURCE:
        ( A ) ORGANISM: HUMAN
        ( H ) CELL LINE: HUMAN T LYMPHOCYTE ( i x ) FEATURE:
        ( A ) NAME/KEY: IGR b 05
        ( D ) OTHER INFORMATION: V BETA w24

( x i ) SEQUENCE DESCRIPTION: SEQ ID NO:5:

```
         TTCCTGTAT  GGGGTGGTAT  TCCTGCC ATG GGT CCT GGG CTT CTC CAC        48
                                        Met Gly Pro Gly Leu Leu His
                                         1               5

TGG ATG GCC CTT TGT CTC CTT GGA ACA GGT CAT GGG GAT GCC ATG GTC            96
Trp Met Ala Leu Cys Leu Leu Gly Thr Gly His Gly Asp Ala Met Val
             10                  15                  20

ATC CAG AAC CCA AGA TAC CAG GTT ACC CAG TTT GGA AAG CCA GTG ACC           144
```

```
Ile Gln Asn Pro Arg Tyr Gln Val Thr Gln Phe Gly Lys Pro Val Thr
 25              30                  35

CTG AGT TGT TCT CAG ACT TTG AAC CAT AAC GTC ATG TAC TGG TAC CAG        192
Leu Ser Cys Ser Gln Thr Leu Asn His Asn Val Met Tyr Trp Tyr Gln
 40              45                  50                  55

CAG AAG TCA AGT CAG GCC CCA AAG CTG CTG TTC CAC TAC TAT GAC AAA        240
Gln Lys Ser Ser Gln Ala Pro Lys Leu Leu Phe His Tyr Tyr Asp Lys
                 60                  65                  70

GAT TTT AAC AAT GAA GCA GAC ACC CCT GAT AAC TTC CAA TCC AGG AGG        288
Asp Phe Asn Asn Glu Ala Asp Thr Pro Asp Asn Phe Gln Ser Arg Arg
             75                  80                  85

CCG AAC ACT TCT TTC TGC TTT CTT GAC ATC CGC TCA CCA GGC CTG GGG        336
Pro Asn Thr Ser Phe Cys Phe Leu Asp Ile Arg Ser Pro Gly Leu Gly
         90                  95                 100

GAC GCA GCC ATG TAC CTG TGT GCC ACC AGC                                366
Asp Ala Ala Met Tyr Leu Cys Ala Thr Ser
    105                 110

( 2 ) INFORMATION FOR SEQ ID NO:6:

( i ) SEQUENCE CHARACTERISTICS:
              ( A ) LENGTH: 238
              ( B ) TYPE: NUCLEOTIDE
              ( C ) STRANDEDNESS: DOUBLE
              ( D ) TOPOLOGY: LINEAR ( i i ) MOLECULE TYPE: cDNA TO mRNA ( v i ) ORIGINAL SOURCE:
              ( A ) ORGANISM: HUMAN
              ( H ) CELL LINE: HUMAN T LYMPHOCYTE ( i x ) FEATURE:
              ( A ) NAME/KEY: IGR b 06
              ( D ) OTHER INFORMATION: V BETA 5

( x i ) SEQUENCE DESCRIPTION: SEQ ID NO:6:

A GGA CAG CAA GCG ACT CTG AGA TGC TCT CCT ATC TCT GGG CAC ACC        46
    Gly Gln Gln Ala Thr Leu Arg Cys Ser Pro Ile Ser Gly His Thr
     1               5                  10                  15

AGT GTG TAC TGG TAC CAA CAG GCC CTG GGT CTG GGC CTC CAG CTC CTC        94
Ser Val Try Trp Tyr Gln Gln Ala Leu Gly Leu Gly Leu Gln Leu Leu
             20                  25                  30

CTT TGG TAT GAC GAG GGT GAA GAG AGA AAC AGA GGA AAC TTC CCT CCT        142
Leu Trp Tyr Asp Glu Gly Glu Glu Arg Asn Arg Gly Asn Phe Pro Pro
         35                  40                  45

AGA TTT TCA GGT CGC CAG TTC CCT AAT TAT AGC TCT GAG CTG AAT GTG        190
Arg Phe Ser Gly Arg Gln Phe Pro Asn Tyr Ser Ser Glu Leu Asn Val
     50                  55                  60

AAC GCC TTG GAG CTG GAG GAC TCG GCC CTG TAT CTC TGT GCC AGC AGC        238
Asn Ala Leu Glu Leu Glu Asp Ser Ala Leu Tyr Leu Cys Ala Ser Ser
 65                  70                  75

( 2 ) INFORMATION FOR SEQ ID NO:7:

( i ) SEQUENCE CHARACTERISTICS:
              ( A ) LENGTH: 192
              ( B ) TYPE: NUCLEOTIDE
              ( C ) STRANDEDNESS: DOUBLE
              ( D ) TOPOLOGY: LINEAR ( i i ) MOLECULE TYPE: cDNA TO mRNA ( v i ) ORIGINAL SOURCE:
              ( A ) ORGANISM: HUMAN
              ( H ) CELL LINE: HUMAN T LYMPHOCYTE ( i x ) FEATURE:
```

(A) NAME/KEY: IGR b 07
(D) OTHER INFORMATION: V BETA 5

(xi) SEQUENCE DESCRIPTION: SEQ ID NO:7:

| ACT | GTG | TCC | TGG | TAC | CAA | CAG | GCC | CTG | GGT | CAG | GGG | CCC | CAG | TTT | ATC | 48 |
| Thr | Val | Ser | Trp | Tyr | Gln | Gln | Ala | Leu | Gly | Gln | Gly | Pro | Gln | Phe | Ile | |
| 1 | | | | 5 | | | | | 10 | | | | | 15 | | |

| TTT | CAG | TAT | TAT | AGG | GAG | GAA | GAG | AAT | GGC | AGA | GGA | AAC | TCC | CCT | CCT | 96 |
| Phe | Gln | Tyr | Tyr | Arg | Glu | Glu | Glu | Asn | Gly | Arg | Gly | Asn | Ser | Pro | Pro | |
| | | | 20 | | | | | 25 | | | | | 30 | | | |

| AGA | TTC | TCA | GGT | CTC | CAG | TTC | CCT | AAT | TAT | AGC | TCT | GAG | CTG | AAT | GTG | 144 |
| Arg | Phe | Ser | Gly | Leu | Gln | Phe | Pro | Asn | Tyr | Ser | Ser | Glu | Leu | Asn | Val | |
| | | 35 | | | | 40 | | | | | 45 | | | | | |

| AAC | GCC | TTG | GAG | CTG | GAC | GAC | TCG | GCC | CTG | TAT | CTC | TGT | GCC | AGC | AGC | 192 |
| Asn | Ala | Leu | Glu | Leu | Asp | Asp | Ser | Ala | Leu | Tyr | Leu | Cys | Ala | Ser | Ser | |
| | 50 | | | | | 55 | | | | | 60 | | | | | |

(2) INFORMATION FOR SEQ ID NO:8:

(i) SEQUENCE CHARACTERISTICS:
(A) LENGTH: 410
(B) TYPE: NUCLEOTIDE
(C) STRANDEDNESS: DOUBLE
(D) TOPOLOGY: LINEAR (ii) MOLECULE TYPE: cDNA TO mRNA (vi) ORIGINAL SOURCE:
(A) ORGANISM: HUMAN
(H) CELL LINE: HUMAN T LYMPHOCYTE (ix) FEATURE:
(A) NAME/KEY: IGR b 08
(D) OTHER INFORMATION: V BETA 5

(xi) SEQUENCE DESCRIPTION: SEQ ID NO:8:

| | | GAACTCACTG | GGTTCTTCCC | CAGGAGGACC | AAGCCCTGAA | TCAGGTGCAG | | | 50 |
| | | TGCTGCCTGC | CCCACTGTGC | C ATG | GGC | CCT | GGG | CTC | CTC | TGC | TGG | 95 |
| | | | | Met | Gly | Pro | Gly | Leu | Leu | Cys | Trp | |
| | | | | 1 | | | | 5 | | | | |

| GTG | CTG | CTT | TGT | CTC | CTG | GGA | GCA | GGC | CCA | GTG | GAC | GCT | GGA | GTC | ACC | 143 |
| Val | Leu | Leu | Cys | Leu | Leu | Gly | Ala | Gly | Pro | Val | Asp | Ala | Gly | Val | Thr | |
| | 10 | | | | | 15 | | | | | 20 | | | | | |

| CAA | AGT | CCC | ACA | CAC | CTG | ATC | AAA | ACG | AGA | GGA | CAG | CAA | GTG | ACT | CTG | 191 |
| Gln | Ser | Pro | Thr | His | Leu | Ile | Lys | Thr | Arg | Gly | Gln | Gln | Val | Thr | Leu | |
| 25 | | | | | 30 | | | | | 35 | | | | | 40 | |

| AGA | TGC | TCT | CCT | ATC | TCT | GAG | CAC | AAG | AGT | GTG | TCC | TGG | TAC | CAA | CAG | 239 |
| Arg | Cys | Ser | Pro | Ile | Ser | Glu | His | Lys | Ser | Val | Ser | Trp | Tyr | Gln | Gln | |
| | | | | 45 | | | | | 50 | | | | | 55 | | |

| GTC | CTG | GGT | CAG | GGG | CCC | CAG | TTT | ATC | TTT | CAG | TAT | TAT | GAG | AAA | GAA | 287 |
| Val | Leu | Gly | Gln | Gly | Pro | Gln | Phe | Ile | Phe | Gln | Tyr | Tyr | Glu | Lys | Glu | |
| | | | 60 | | | | | 65 | | | | | 70 | | | |

| GAG | AGA | GGA | AGA | GGA | AAC | TTC | CCT | GAT | CGA | TTC | TCA | GCT | CGC | CAG | TTC | 335 |
| Glu | Arg | Gly | Arg | Gly | Asn | Phe | Pro | Asp | Arg | Phe | Ser | Ala | Arg | Gln | Phe | |
| | | 75 | | | | | 80 | | | | | 85 | | | | |

| CCT | AAC | TAT | AGC | TCT | GAG | CTG | AAT | GTG | AAC | GCC | TTG | TTG | CTG | GGG | GAC | 383 |
| Pro | Asn | Tyr | Ser | Ser | Glu | Leu | Asn | Val | Asn | Ala | Leu | Leu | Leu | Gly | Asp | |
| | 90 | | | | | 95 | | | | | 100 | | | | | |

| TCG | GCC | CTG | TAT | CTC | TGT | GCC | AGC | AGC | | | | | | | | 410 |
| Ser | Ala | Leu | Tyr | Leu | Cys | Ala | Ser | Ser | | | | | | | | |
| 105 | | | | | 110 | | | | | | | | | | | |

(2) INFORMATION FOR SEQ ID NO:9:

(i) SEQUENCE CHARACTERISTICS:

(A) LENGTH: 380
(B) TYPE: NUCLEOTIDE
(C) STRANDEDNESS: DOUBLE
(D) TOPOLOGY: LINEAR (i i) MOLECULE TYPE: cDNA TO mRNA (v i) ORIGINAL SOURCE:
(A) ORGANISM: HUMAN
(H) CELL LINE: HUMAN T LYMPHOCYTE (i x) FEATURE:
(A) NAME/KEY: IGR b 09
(D) OTHER INFORMATION: V BETA 5

(x i) SEQUENCE DESCRIPTION: SEQ ID NO:9:

```
            AAGCCCTGAA TCAGATGCAG TGCTTCCTGT CCCTCTGTGC C ATG GGC           47
                                                          Met Gly
                                                          1

CCC GGG CTC CTC TGC TGG GCA CTG CTT TGT CTC CTG GGA GCA GGC TTA            95
Pro Gly Leu Leu Cys Trp Ala Leu Leu Cys Leu Leu Gly Ala Gly Leu
        5               10                  15

GTG GAC GCT GGA GTC ACC CAA AGT CCC ACA CAC CTG ATC AAA ACG AGA           143
Val Asp Ala Gly Val Thr Gln Ser Pro Thr His Leu Ile Lys Thr Arg
    20              25                  30

GGA CAG CAA GTG ACT CTG AGA TGC TCT CCT AAG TCT GGG CAT GAC ACT           191
Gly Gln Gln Val Thr Leu Arg Cys Ser Pro Lys Ser Gly His Asp Thr
35              40                  45                      50

GTG TCC TGG TAC CAA CAG GCC CTG GGT CAG GGG CCC CAG TTT ATC TTT           239
Val Ser Trp Tyr Gln Gln Ala Leu Gly Gln Gly Pro Gln Phe Ile Phe
                55                  60                  65

CAG TAT TAT GAG GAG GAA GAG AGA CAG AGA GGC AAC TTC CCT GAT CGA           287
Gln Tyr Tyr Glu Glu Glu Glu Arg Gln Arg Gly Asn Phe Pro Asp Arg
                70                  75                  80

TTC TCA GGT CAC CAG TTC CCT AAC TAT AGC TCT GAG CTG AAT GTG AAC           335
Phe Ser Gly His Gln Phe Pro Asn Tyr Ser Ser Glu Leu Asn Val Asn
            85                  90                  95

GCC TTG TTG CTG GGG GAC TCG GCC CTC TAT CTC TGT GCC AGC AGC                380
Ala Leu Leu Leu Gly Asp Ser Ala Leu Tyr Leu Cys Ala Ser Ser
        100                 105                 110
```

(2) INFORMATION FOR SEQ ID NO:10:

(i) SEQUENCE CHARACTERISTICS:
(A) LENGTH: 351
(B) TYPE: NUCLEOTIDE
(C) STRANDEDNESS: DOUBLE
(D) TOPOLOGY: LINEAR (i i) MOLECULE TYPE: cDNA TO mRNA (v i) ORIGINAL SOURCE:
(A) ORGANISM: HUMAN
(H) CELL LINE: HUMAN T LYMPHOCYTE (i x) FEATURE:
(A) NAME/KEY: IGR b 11
(D) OTHER INFORMATION: V BETA 6

(x i) SEQUENCE DESCRIPTION: SEQ ID NO:10:

```
        GACCCTGCC ATG GGC ACC AGT CTC CTA TGC TGG GTG GTC CTG GGT TTC        48
                  Met Gly Thr Ser Leu Leu Cys Trp Val Val Leu Gly Phe
                  1               5                   10

CTA GGG ACA GAT CAC ACA GGT GCT GGA GTC TCC CAG TCT CCC AGG TAC            96
Leu Gly Thr Asp His Thr Gly Ala Gly Val Ser Gln Ser Pro Arg Tyr
        15                  20                  25

AAA GTC ACA AAG AGG GGA CAG GAT GTA GCT CTC AGG TGT GAT CCA ATC           144
Gln Val Thr Lys Arg Gly Gln Asp Val Ala Leu Arg Cys Asp Pro Ile
```

```
                30                         35                              40                              45
         TCG GGT CAT GTA TCC CTT TAT TGG TAC CGA CAG GCC CTG GGG CAG GGC        192
         Ser Gly His Val Ser Leu Tyr Trp Tyr Arg Gln Ala Leu Gly Gln Gly
                          50                  55                      60

CCA GAG TTT CTG ACT TAC TTC AAT TAT GAA GCC CAA CAA GAC AAA TCA        240
         Pro Glu Phe Leu Thr Tyr Phe Asn Tyr Glu Ala Gln Gln Asp Lys Ser
                     65                  70                      75

GGG CTG CCC AAT GAT CGG TTC TCT GCA GAG AGG CCT GAG GGA TCC ATC        288
         Gly Leu Pro Asn Asp Arg Phe Ser Ala Glu Arg Pro Glu Gly Ser Ile
                 80                  85                      90

TCC ACT CTG ACG ATC CAG CGC ACA GAG CAG CGG GAC TCG GCC ATG TAT        336
         Ser Thr Leu Thr Ile Gln Arg Thr Glu Gln Arg Asp Ser Ala Met Tyr
             95                 100                     105

CGC TGT GCC AGC AGC                                                    351
         Arg Cys Ala Ser Ser
         110
```

(2) INFORMATION FOR SEQ ID NO:11:

(i) SEQUENCE CHARACTERISTICS:
        (A) LENGTH: 238
        (B) TYPE: NUCLEOTIDE
        (C) STRANDEDNESS: DOUBLE
        (D) TOPOLOGY: LINEAR (ii) MOLECULE TYPE: cDNA TO mRNA (vi) ORIGINAL SOURCE:
        (A) ORGANISM: HUMAN
        (H) CELL LINE: HUMAN T LYMPHOCYTE (ix) FEATURE:
        (A) NAME/KEY: IGR b 12
        (D) OTHER INFORMATION: V BETA 6

(xi) SEQUENCE DESCRIPTION: SEQ ID NO:11:

```
         A AAG GAT GTA GAG CTC AGG TGT GAT CCA ATT TCA GGT CAT ACT GCC          46
           Lys Asp Val Glu Leu Arg Cys Asp Pro Ile Ser Gly His Thr Ala
           1                 5                  10                   15

CTT TAC TGG TAC CGA CAG AGC CTG GGG CAG GGC CTG GAG TTT TTA ATT        94
         Leu Tyr Trp Tyr Arg Gln Ser Leu Gly Gln Gly Leu Glu Phe Leu Ile
                         20                  25                      30

TAC TTC CAA GGC AAC AGT GCA CCA GAC AAA TCA GGG CTG CCC AAC GAT        142
         Tyr Phe Gln Gly Asn Ser Ala Pro Asp Lys Ser Gly Leu Pro Asn Asp
                     35                  40                      45

CGG TTC TTT GCA GTC AGG CCT GAG GGA TCC GTC TCT ACT CTG AGG ATC        190
         Arg Phe Phe Ala Val Arg Pro Glu Gly Ser Val Ser Thr Leu Arg Ile
                 50                  55                      60

CAG CGC ACA GAG CGG GGG GAC TCA GCC GTG TAT CTC TGT GCC AGC AGC        238
         Gln Arg Thr Glu Arg Gly Asp Ser Ala Val Tyr Leu Cys Ala Ser Ser
             65                  70                      75
```

(2) INFORMATION FOR SEQ ID NO:12:

(i) SEQUENCE CHARACTERISTICS:
        (A) LENGTH: 294
        (B) TYPE: NUCLEOTIDE
        (C) STRANDEDNESS: DOUBLE
        (D) TOPOLOGY: LINEAR (ii) MOLECULE TYPE: cDNA TO mRNA (vi) ORIGINAL SOURCE:
        (A) ORGANISM: HUMAN
        (H) CELL LINE: HUMAN T LYMPHOCYTE (ix) FEATURE:
        (A) NAME/KEY: IGR b 13
        (D) OTHER INFORMATION: V BETA 12

( x i ) SEQUENCE DESCRIPTION: SEQ ID NO:12:

| | | | | | | | | | | | | | | | | |
|---|---|---|---|---|---|---|---|---|---|---|---|---|---|---|---|---|
| TCA | GGA | CAC | AGG | GAT | GCT | GAA | ATC | ACC | CAG | AGC | CCA | AGA | CAC | AAG | ATC | 48 |
| Ser | Gly | His | Arg | Asp | Ala | Glu | Ile | Thr | Gln | Ser | Pro | Arg | His | Lys | Ile | |
| 1 | | | | 5 | | | | | 10 | | | | | 15 | | |
| ACA | GAG | ACA | GGA | AGG | CAG | GTG | ACC | TTG | GCG | TGT | CAC | CAG | ACT | TGG | AAC | 96 |
| Thr | Glu | Thr | Gly | Arg | Gln | Val | Thr | Leu | Ala | Cys | His | Gln | Thr | Trp | Asn | |
| | | | 20 | | | | | 25 | | | | | 30 | | | |
| CAC | AAC | AAT | ATG | TTC | TGG | TAT | CGA | CAA | GAC | CTG | GGA | CAT | GGG | CTG | AGG | 144 |
| His | Asn | Asn | Met | Phe | Trp | Tyr | Arg | Gln | Asp | Leu | Gly | His | Gly | Leu | Arg | |
| | | 35 | | | | | 40 | | | | | 45 | | | | |
| CTG | ATC | CAT | TAC | TCA | TAT | GGT | GTT | CAA | GAC | ACT | AAC | AAA | GGA | GAA | GTC | 192 |
| Leu | Ile | His | Tyr | Ser | Tyr | Gly | Val | Gln | Asp | Thr | Asn | Lys | Gly | Glu | Val | |
| | 50 | | | | 55 | | | | | 60 | | | | | | |
| TCA | GAT | GGC | TAC | AGT | GTC | TCT | AGA | TCA | AAC | ACA | GAG | GAC | CTC | CCC | CTC | 240 |
| Ser | Asp | Gly | Tyr | Ser | Val | Ser | Arg | Ser | Asn | Thr | Glu | Asp | Leu | Pro | Leu | |
| 65 | | | | | 70 | | | | | 75 | | | | | 80 | |
| ACT | CTG | GAG | TCT | GCT | GCC | TCC | TCC | CAG | ACA | TCT | GTA | TAT | TTC | TGC | GCC | 288 |
| Thr | Leu | Glu | Ser | Ala | Ala | Ser | Ser | Gln | Thr | Ser | Val | Tyr | Phe | Cys | Ala | |
| | | | | 85 | | | | | 90 | | | | | 95 | | |
| AGC | AGG | | | | | | | | | | | | | | | 294 |
| Ser | Ser | | | | | | | | | | | | | | | |

( 2 ) INFORMATION FOR SEQ ID NO:13:

( i ) SEQUENCE CHARACTERISTICS:
( A ) LENGTH: 369
( B ) TYPE: NUCLEOTIDE
( C ) STRANDEDNESS: DOUBLE
( D ) TOPOLOGY: LINEAR ( i i ) MOLECULE TYPE: cDNA TO mRNA ( v i ) ORIGINAL SOURCE:
( A ) ORGANISM: HUMAN
( H ) CELL LINE: HUMAN T LYMPHOCYTE ( i x ) FEATURE:
( A ) NAME/KEY: IGR b 14
( D ) OTHER INFORMATION: V BETA 13

( x i ) SEQUENCE DESCRIPTION: SEQ ID NO:13:

| | | | | | | | | | | | | | | | | |
|---|---|---|---|---|---|---|---|---|---|---|---|---|---|---|---|---|
| AGAAGACCCC | TCCATCCTGT | AGCACCTGCC | ATG | AGC | ATC | GGG | CTC | CTG | | | | | | | | 48 |
| | | | Met | Ser | Ile | Gly | Leu | Leu | | | | | | | | |
| | | | 1 | | | | 5 | | | | | | | | | |
| TGC | TGT | GTG | GCC | TTT | TCT | CTC | CTG | TGG | GCA | AGT | CCA | GTG | AAT | GCT | GGT | 96 |
| Cys | Cys | Val | Ala | Phe | Ser | Leu | Leu | Trp | Ala | Ser | Pro | Val | Asn | Ala | Gly | |
| | | | 10 | | | | | 15 | | | | | 20 | | | |
| GTC | ACT | CAG | ACC | CCA | AAA | TTC | CAG | GTC | CTG | AAG | ACA | GGA | CAG | AGC | ATG | 144 |
| Val | Thr | Gln | Thr | Pro | Lys | Phe | Gln | Val | Leu | Lys | Thr | Gly | Gln | Ser | Met | |
| | | 25 | | | | | 30 | | | | | 35 | | | | |
| ACA | CTG | CAG | TGT | GCC | CAG | GAT | ATG | AAC | CAT | AAC | TCC | ATG | TAC | TGG | TAT | 192 |
| Thr | Leu | Gln | Cys | Ala | Gln | Asp | Met | Asn | His | Asn | Ser | Met | Tyr | Trp | Tyr | |
| | 40 | | | | 45 | | | | | 50 | | | | | | |
| CGA | CAA | GAC | CCA | GGC | ATG | GGA | CTG | AGG | CTG | ATT | TAT | TAC | TCA | GCT | TCT | 240 |
| Arg | Gln | Asp | Pro | Gly | Met | Gly | Leu | Arg | Leu | Ile | Tyr | Tyr | Ser | Ala | Ser | |
| 55 | | | | | 60 | | | | | 65 | | | | | 70 | |
| GAG | GGT | ACC | ACT | GAC | AAA | GGA | GAA | GTC | CCC | AAT | GGC | TAC | AAT | GTC | TCC | 288 |
| Glu | Gly | Thr | Thr | Asp | Lys | Gly | Glu | Val | Pro | Asn | Gly | Tyr | Asn | Val | Ser | |
| | | | | 75 | | | | | 80 | | | | | 85 | | |
| AGA | TTA | AAC | AAA | CGG | GAG | TTC | TCG | CTC | AGG | CTG | GAG | TCG | GCT | GCT | CCC | 336 |
| Arg | Leu | Asn | Lys | Arg | Glu | Phe | Ser | Leu | Arg | Leu | Glu | Ser | Ala | Ala | Pro | |
| | | | 90 | | | | | 95 | | | | | 100 | | | |
| TCC | CAG | ACA | TCT | GTG | TAC | TTC | TGT | GCC | AGC | ACC | | | | | | 369 |

Ser Gln Thr Ser Val Tyr Phe Cys Ala Ser Thr
        105                 110

(2) INFORMATION FOR SEQ ID NO:14:

(i) SEQUENCE CHARACTERISTICS:
        (A) LENGTH: 356
        (B) TYPE: NUCLEOTIDE
        (C) STRANDEDNESS: DOUBLE
        (D) TOPOLOGY: LINEAR (ii) MOLECULE TYPE: cDNA TO mRNA (vi) ORIGINAL SOURCE:
        (A) ORGANISM: HUMAN
        (H) CELL LINE: HUMAN T LYMPHOCYTE (ix) FEATURE:
        (A) NAME/KEY: IGR b 15
        (D) OTHER INFORMATION: V BETA 13

(xi) SEQUENCE DESCRIPTION: SEQ ID NO:14:

```
        TGCTTGTAGC ATCTGCC ATG AGA ATC AGG CTC CTG TGC TGT GTG GCC         47
                           Met Arg Ile Arg Leu Leu Cys Cys Val Ala
                           1               5                   10

TTT TCT CTC CTG TGG GCA GGT CCA GTG ATT GCT GGG ATC ACC CAG GCA           95
Phe Ser Leu Leu Trp Ala Gly Pro Val Ile Ala Gly Ile Thr Gln Ala
                15              20                  25

CCA ACA TCT CAG ATC CTG GCA GCA GGA CGG CGC ATG ACA CTG AGA TGT          143
Pro Thr Ser Gln Ile Leu Ala Ala Gly Arg Arg Met Thr Leu Arg Cys
            30                  35                  40

ACC CAG GAT ATG AGA CAT AAT GCC ATG TAC TGG TAT AGA CAA GAT CTA          191
Thr Gln Asp Met Arg His Asn Ala Met Tyr Trp Tyr Arg Gln Asp Leu
            45                  50                  55

GGA CTG GGG CTA AGG CTC ATC CAT TAT TCA AAT ACT GCA GGT ACC ACT          239
Gly Leu Gly Leu Arg Leu Ile His Tyr Ser Asn Thr Ala Gly Thr Thr
        60                  65                  70

GGC AAA GGA GAA GTC CCT GAT GGT TAT AGT GTC TCC AGA GCA AAC ACA          287
Gly Lys Gly Glu Val Pro Asp Gly Tyr Ser Val Ser Arg Ala Asn Thr
75                  80                  85                  90

GAT GAT TTC CCC CTC ACG TTG GCG TCT GCT GTA CCC TCT CAG ACA TCT          335
Asp Asp Phe Pro Leu Thr Leu Ala Ser Ala Val Pro Ser Gln Thr Ser
                95              100                 105

GTG TAC TTC TGT GCC AGC AGT                                              356
Val Tyr Phe Cys Ala Ser Ser
                110
```

(2) INFORMATION FOR SEQ ID NO:15:

(i) SEQUENCE CHARACTERISTICS:
        (A) LENGTH: 345
        (B) TYPE: NUCLEOTIDE
        (C) STRANDEDNESS: DOUBLE
        (D) TOPOLOGY: LINEAR (ii) MOLECULE TYPE: cDNA TO mRNA (vi) ORIGINAL SOURCE:
        (A) ORGANISM: HUMAN
        (H) CELL LINE: HUMAN T LYMPHOCYTE (ix) FEATURE:
        (A) NAME/KEY: IGR b 16
        (D) OTHER INFORMATION: V BETA (xi) SEQUENCE DESCRIPTION: SEQ ID NO:15:

```
        AAGGCCCAGC CCCTTTCCAT TGGGGCTGCA GCATCAGCTG TTTCCTTCTC             50

TGCAGGT CCA GTG AAT GCT GGT GTC ACT CAG ACC CCA AAA TTC CGC              96
```

|  |  |  | Pro Val Asn Ala Gly Val Thr Gln Thr Pro Lys Phe Arg |  |  |  |  |  |  |  |  |  |  |
|---|---|---|---|---|---|---|---|---|---|---|---|---|---|
|  |  |  | 1 | | | 5 | | | | 10 | | | |

```
ATC CTG AAG ATA GGA CAG AGC ATG ACA CTG CAG TGT GCC CAG GAT ATG      144
Ile Leu Lys Ile Gly Gln Ser Met Thr Leu Gln Cys Ala Gln Asp Met
        15              20                  25

AAC CAT AAC TAC ATG TAC TGG TAT CGA CAA GAC CCA GGC ATG GGG CTG      192
Asn His Asn Tyr Met Tyr Trp Tyr Arg Gln Asp Pro Gly Met Gly Leu
30                  35                  40                  45

AAG CTG ATT TAT TAT TCA GTT GGT GCT GGT ATC ACT GAT AAA GGA GAA      240
Lys Leu Ile Tyr Tyr Ser Val Gly Ala Gly Ile Thr Asp Lys Gly Glu
                    50              55                  60

GTC CCG AAT GGC TAC AAC GTC TCC AGA TCA ACC ACA GAG GAT TTC CCG      288
Val Pro Asn Gly Tyr Asn Val Ser Arg Ser Thr Thr Glu Asp Phe Pro
                65                  70                  75

CTC AGG CTG GAG TTG GCT GCT CCC TCC CAG ACA TCT GTG TAC TTC TGT      336
Leu Arg Leu Glu Leu Ala Ala Pro Ser Gln Thr Ser Val Tyr Phe Cys
            80                  85                  90

GCC AGC AGT                                                          345
Ala Ser Ser
95
```

( 2 ) INFORMATION FOR SEQ ID NO:16:

( i ) SEQUENCE CHARACTERISTICS:
        ( A ) LENGTH: 450
        ( B ) TYPE: NUCLEOTIDE
        ( C ) STRANDEDNESS: DOUBLE
        ( D ) TOPOLOGY: LINEAR ( i i ) MOLECULE TYPE: cDNA TO mRNA ( v i ) ORIGINAL SOURCE:
        ( A ) ORGANISM: HUMAN
        ( H ) CELL LINE: HUMAN T LYMPHOCYTE ( i x ) FEATURE:
        ( A ) NAME/KEY: IGR b 17
        ( D ) OTHER INFORMATION: V BETA 7

( x i ) SEQUENCE DESCRIPTION: SEQ ID NO:16:

```
            TGGAGCAGTG ACATCACAGG AAAAACCACC AACCAAGGCC       40
AAGGAGACCA GAGCCCAGCA CCTCACCCAG AGGACCCCAG TCAGAGGCCC CATCTCAGAC  100

CCGAGGCTAG C ATG GGC TGC AGG CTG CTC TGC TGT GCG GTT CTC   144
                     Met Gly Cys Arg Leu Leu Cys Cys Ala Val Leu
                      1               5                   10

TGT CTC CTG GGA GCG GTC CCC ATG GAA ACG GGA GTT ACG CAG ACA CCA      192
Cys Leu Leu Gly Ala Val Pro Met Glu Thr Gly Val Thr Gln Thr Pro
            15                  20                  25

AGA CAC CTG GTC ATG GGA ATG ACA AAT AAG AAG TCT TTG AAA TGT GAA      240
Arg His Leu Val Met Gly Met Thr Asn Lys Lys Ser Leu Lys Cys Glu
        30                  35                  40

CAA CAT CTG GGG CAT AAC GCT ATG TAT TGG TAC AAG CAA AGT GCT AAG      288
Gln His Leu Gly His Asn Ala Met Tyr Trp Tyr Lys Gln Ser Ala Lys
    45                  50                  55

AAG CCA CTG GAG CTC ATG TTT GTC TAC AAC TTT AAA GAA CAG ACT GAA      336
Lys Pro Leu Glu Leu Met Phe Val Tyr Asn Phe Lys Glu Gln Thr Glu
60              65                  70                  75

AAC AAC AGT GTG CCA AGT CGC TTC TCA CCT GAA TGC CCC AAC AGC TCT      384
Asn Asn Ser Val Pro Ser Arg Phe Ser Pro Glu Cys Pro Asn Ser Ser
                80                  85                  90

CAC TTA TGC CTT CAC CTA CAC ACC CTG CAG CCA GAA GAC TCG GCC CTG      432
His Leu Cys Leu His Leu His Thr Leu Gln Pro Glu Asp Ser Ala Leu
                95                  100                 105
```

```
TAT CTC TGT GCC AGC ACC                                                                             450
Tyr Leu Cys Ala Ser Thr
            110
```

( 2 ) INFORMATION FOR SEQ ID NO:17:

( i ) SEQUENCE CHARACTERISTICS:
        ( A ) LENGTH: 354
        ( B ) TYPE: NUCLEOTIDE
        ( C ) STRANDEDNESS: DOUBLE
        ( D ) TOPOLOGY: LINEAR ( i i ) MOLECULE TYPE: cDNA TO mRNA ( v i ) ORIGINAL SOURCE:
        ( A ) ORGANISM: HUMAN
        ( H ) CELL LINE: HUMAN T LYMPHOCYTE ( i x ) FEATURE:
        ( A ) NAME/KEY: IGR b 18
        ( D ) OTHER INFORMATION: V BETA 7

( x i ) SEQUENCE DESCRIPTION: SEQ ID NO:17:

```
          AGACCCGAGG CTAGC ATG GGC TGC AGG CTG CTC TGC TCT GCG GTT CTC      48
                          Met Gly Cys Arg Leu Leu Cys Ser Ala Val Leu
                           1           5                      10

TGT CTC CTG GGA GCG GTC CCC ATG GAA ACG GGA GTT ACG CAG ACA CCA             96
Cys Leu Leu Gly Ala Val Pro Met Glu Thr Gly Val Thr Gln Thr Pro
                15              20              25

AGA CAC CTG GTC ATG GGA ATG ACA AAT AAG AAG TCT TTG AAA TGT GAA            144
Arg His Leu Val Met Gly Met Thr Asn Lys Lys Ser Leu Lys Cys Glu
            30              35              40

CAA CAT CTG GGT CAT AAC GCT ATG TAT TGG TAC AAG CAA AGT GCT AAG            192
Gln His Leu Gly His Asn Ala Met Tyr Trp Tyr Lys Gln Ser Ala Lys
        45              50              55

AAG CCA CTG GAG CTC ATG TTT GTC TAC AGT CTT GAA GAA CGG GTT GAA            240
Lys Pro Leu Glu Leu Met Phe Val Tyr Ser Leu Glu Glu Arg Val Glu
 60              65              70                          75

AAC AAC AGT GTG CCA AGT CGC TTC TCA CCT GAA TGC CCC AAC AGC TCT            288
Asn Asn Ser Val Pro Ser Arg Phe Ser Pro Glu Cys Pro Asn Ser Ser
                80              85              90

CAC TTA TCC CTT CAC CTA CAC ACC CTG CAG CCA GAA GAC TCG GCC CTG            336
His Leu Ser Leu His Leu His Thr Leu Gln Pro Glu Asp Ser Ala Leu
            95              100             105

TAT CTC TGC GCC AGC AGC                                                    354
Tyr Leu Cys Ala Ser Ser
            110
```

( 2 ) INFORMATION FOR SEQ ID NO:18:

( i ) SEQUENCE CHARACTERISTICS:
        ( A ) LENGTH: 368
        ( B ) TYPE: NUCLEOTIDE
        ( C ) STRANDEDNESS: DOUBLE
        ( D ) TOPOLOGY: LINEAR ( i i ) MOLECULE TYPE: cDNA TO mRNA ( v i ) ORIGINAL SOURCE:
        ( A ) ORGANISM: HUMAN
        ( H ) CELL LINE: HUMAN T LYMPHOCYTE ( i x ) FEATURE:
        ( A ) NAME/KEY: IGR b 19
        ( D ) OTHER INFORMATION: V BETA 7

( x i ) SEQUENCE DESCRIPTION: SEQ ID NO:18:

```
          AGAGGCCCCA TCTCAGACCC GAGGCTAGC ATG GGC TGC AGG CTG CTC           47
                                         Met Gly Cys Arg Leu Leu
```

| | | | | | | | | | | | | | | | | |
|---|---|---|---|---|---|---|---|---|---|---|---|---|---|---|---|---|
| TGC | TGT | GCG | GTT | CTC | TGT | CTC | CTG | GGA | GCA | GTT | CCC | ATA | GAC | ACT | GAA | 95 |
| Cys | Cys | Ala | Val | Leu | Cys | Leu | Leu | Gly | Ala | Val | Pro | Ile | Asp | Thr | Glu | |
| | | 10 | | | | | 15 | | | | | | 20 | | | |
| GTT | ACC | CAG | ACA | CCA | AAA | CAC | CTG | GTC | ATG | GGA | ATG | ACA | AAT | AAG | AAG | 143 |
| Val | Thr | Gln | Thr | Pro | Lys | His | Leu | Val | Met | Gly | Met | Thr | Asn | Lys | Lys | |
| | | 25 | | | | | 30 | | | | | 35 | | | | |
| TCT | TTG | AAA | TGT | GAA | CAA | CAT | ATG | GGG | CAC | AGG | GCT | ATG | TAT | TGG | TAC | 191 |
| Ser | Leu | Lys | Cys | Glu | Gln | His | Met | Gly | His | Arg | Ala | Met | Tyr | Trp | Tyr | |
| | 40 | | | | | 45 | | | | | 50 | | | | | |
| AAG | CAG | AAA | GCT | AAG | AAG | CCA | CCG | GAG | CTC | ATG | TTT | GTC | TAC | AGC | TAT | 239 |
| Lys | Gln | Lys | Ala | Lys | Lys | Pro | Pro | Glu | Leu | Met | Phe | Val | Tyr | Ser | Tyr | |
| 55 | | | | | 60 | | | | | 65 | | | | | 70 | |
| GAG | AAA | CTC | TCT | ATA | AAT | GAA | AGT | GTG | CCA | AGT | CGC | TTC | TCA | CCT | GAA | 287 |
| Glu | Lys | Leu | Ser | Ile | Asn | Glu | Ser | Val | Pro | Ser | Arg | Phe | Ser | Pro | Glu | |
| | | | | 75 | | | | | 80 | | | | | 85 | | |
| TGC | CCC | AAC | AGC | TCT | CTC | TTA | AAC | CTT | CAC | CTA | CAC | GCC | CTG | CAG | CCA | 335 |
| Cys | Pro | Asn | Ser | Ser | Leu | Leu | Asn | Leu | His | Leu | His | Ala | Leu | Gln | Pro | |
| | | | 90 | | | | | 95 | | | | | 100 | | | |
| GAA | GAC | TCA | GCC | CTG | TAT | CTC | TGC | GCC | AGC | AGC | | | | | | 368 |
| Glu | Asp | Ser | Ala | Leu | Tyr | Leu | Cys | Ala | Ser | Ser | | | | | | |
| | | 105 | | | | | 110 | | | | | | | | | |

( 2 ) INFORMATION FOR SEQ ID NO:19:

( i ) SEQUENCE CHARACTERISTICS:
        ( A ) LENGTH: 432
        ( B ) TYPE: NUCLEOTIDE
        ( C ) STRANDEDNESS: DOUBLE
        ( D ) TOPOLOGY: LINEAR ( i i ) MOLECULE TYPE: cDNA TO mRNA ( v i ) ORIGINAL SOURCE:
        ( A ) ORGANISM: HUMAN
        ( H ) CELL LINE: HUMAN T LYMPHOCYTE ( i x ) FEATURE:
        ( A ) NAME/KEY: IGR b 20
        ( D ) OTHER INFORMATION: V BETA 9

( x i ) SEQUENCE DESCRIPTION: SEQ ID NO:19:

```
                        ACCTCTCAAC GGCAGTGAAA CCACAGCCTA GTCCTCTCAC          40
CACTGCAGAC CAGAATCCTG CCCTGGGCCT TGCCTGGTCT GCCTCACTCT GCC ATG              96
                                                            MET
                                                            1
```

| | | | | | | | | | | | | | | | | |
|---|---|---|---|---|---|---|---|---|---|---|---|---|---|---|---|---|
| GGC | TGC | AGG | CTC | CTC | TGC | TGT | GTG | GTC | TTC | TGC | CTC | CTC | CAA | GCA | GGT | 144 |
| Gly | Cys | Arg | Leu | Leu | Cys | Cys | Val | Val | Phe | Cys | Leu | Leu | Gln | Ala | Gly | |
| | | | 5 | | | | | 10 | | | | | 15 | | | |
| CCC | TTG | GAC | ACA | GCT | GTT | TCC | CAG | ACT | CCA | AAA | TAC | CTG | GTC | ACA | CAG | 192 |
| Pro | Leu | Asp | Thr | Ala | Val | Ser | Gln | Thr | Pro | Lys | Tyr | Leu | Val | Thr | Gln | |
| | | 20 | | | | | 25 | | | | | 30 | | | | |
| ATG | GGA | AAC | GAC | AAG | TCC | ATT | AAA | TGT | GAA | CAA | AAT | CTG | GGC | CAT | GAT | 240 |
| Met | Gly | Asn | Asp | Lys | Ser | Ile | Lys | Cys | Glu | Gln | Asn | Leu | Gly | His | Asp | |
| | 35 | | | | | 40 | | | | | 45 | | | | | |
| ACT | ATG | TAT | TGG | TAT | AAA | CAG | GAC | TCT | AAG | AAA | TTT | CTG | AAG | ATA | ATG | 288 |
| Thr | Met | Tyr | Trp | Tyr | Lys | Gln | Asp | Ser | Lys | Lys | Phe | Leu | Lys | Ile | Met | |
| 50 | | | | | 55 | | | | | 60 | | | | | 65 | |
| TTT | AGC | TAC | AAT | AAT | AAG | GAG | CTC | ATT | ATA | AAT | GAA | ACA | GTT | CCA | AAT | 336 |
| Phe | Ser | Tyr | Asn | Asn | Lys | Glu | Leu | Ile | Ile | Asn | Glu | Thr | Val | Pro | Asn | |
| | | | | 70 | | | | | 75 | | | | | 80 | | |
| CGC | TTC | TCA | CCT | AAA | TCT | CCA | GAC | AAA | GCT | CAC | TTA | AAT | CTT | CAC | ATC | 384 |
| Arg | Phe | Ser | Pro | Lys | Ser | Pro | Asp | Lys | Ala | His | Leu | Asn | Leu | His | Ile | |
| | | | 85 | | | | | 90 | | | | | 95 | | | |

| AAT | TCC | CTG | GAG | CTT | GGT | GAC | TCT | GCT | GTG | TAT | TTC | TGT | GCC | AGC | AGC | 432 |
| Asn | Ser | Leu | Glu | Leu | Gly | Asp | Ser | Ala | Val | Tyr | Phe | Cys | Ala | Ser | Ser | |
| | | 100 | | | | | 105 | | | | | 110 | | | | |

( 2 ) INFORMATION FOR SEQ ID NO:20:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: PRIMER A ( x i ) SEQUENCE DESCRIPTION: SEQ ID NO:20:

TATCTGGAGT CATTGAGGGC GGGC       24

( 2 ) INFORMATION FOR SEQ ID NO:21:

( i ) SEQUENCE CHARACTERISTICS:
        ( A ) LENGTH: 35
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: POLY C PRIMER ( x i ) SEQUENCE DESCRIPTION: SEQ ID NO:21:

GCATGCGCGC GGCCGCGGAG GCCCCCCCCC CCCCC       35

( 2 ) INFORMATION FOR SEQ ID NO:22:

( i ) SEQUENCE CHARACTERISTICS:
        ( A ) LENGTH: 25
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: PRIMER B ( x i ) SEQUENCE DESCRIPTION: SEQ ID NO:22:

TGTGGCCAGG CATGCCAGTG TGGCC       25

( 2 ) INFORMATION FOR SEQ ID NO:23:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: PRIMER C ( x i ) SEQUENCE DESCRIPTION: SEQ ID NO:23:

GGTGTGGGAG AATTCTGCTT CTGA       24

( 2 ) INFORMATION FOR SEQ ID NO:24:

( i ) SEQUENCE CHARACTERISTICS:
       ( A ) LENGTH: 19
       ( B ) TYPE: NUCLEOTIDE
       ( C ) STRANDEDNESS: SINGLE
       ( D ) TOPOLOGY: LINEAR ( i i ) MOLECULE TYPE: OLIGONUCLEOTIDE ( i x ) FEATURE:
       ( A ) NAME/KEY:
       ( D ) OTHER INFORMATION: OLIGONUCLEOTIDE D ( x i ) SEQUENCE DESCRIPTION: SEQ ID NO:24:

TCTGCTTCTG ATGGCTCAA                                                    19

( 2 ) INFORMATION FOR SEQ ID NO:25:

( i ) SEQUENCE CHARACTERISTICS:
       ( A ) LENGTH: 24
       ( B ) TYPE: NUCLEOTIDE
       ( C ) STRANDEDNESS: SINGLE
       ( D ) TOPOLOGY: LINEAR ( i i ) MOLECULE TYPE: OLIGONUCLEOTIDE ( i x ) FEATURE:
       ( A ) NAME/KEY:
       ( D ) OTHER INFORMATION: TYPE V BETA 1, CLONE HBVT73,
             POSITION 251

( x i ) SEQUENCE DESCRIPTION: SEQ ID NO:25:

CCGCACAACA GTTCCCTGAC TTGC                                              24

( 2 ) INFORMATION FOR SEQ ID NO:26:

( i ) SEQUENCE CHARACTERISTICS:
       ( A ) LENGTH: 24
       ( B ) TYPE: NUCLEOTIDE
       ( C ) STRANDEDNESS: SINGLE
       ( D ) TOPOLOGY: LINEAR ( i i ) MOLECULE TYPE: OLIGONUCLEOTIDE ( i x ) FEATURE:
       ( A ) NAME/KEY:
       ( D ) OTHER INFORMATION: TYPE V BETA 2, CLONE MOLT 4,
             POSITION 210

( x i ) SEQUENCE DESCRIPTION: SEQ ID NO:26:

GGCCACATAC GAGCAAGGCG TCGA                                              24

( 2 ) INFORMATION FOR SEQ ID NO:27:

( i ) SEQUENCE CHARACTERISTICS:
       ( A ) LENGTH: 24
       ( B ) TYPE: NUCLEOTIDE
       ( C ) STRANDEDNESS: SINGLE
       ( D ) TOPOLOGY: LINEAR ( i i ) MOLECULE TYPE: OLIGONUCLEOTIDE ( i x ) FEATURE:
       ( A ) NAME/KEY:
       ( D ) OTHER INFORMATION: TYPE V BETA 3, CLONE DT259,
             POSITION 232*, THE 11TH NUCLEOTIDE CORRESPONDS TO
             MISMATCHES INTRODUCED RELATIVE TO THE NATURAL SEQUENCE ( x i ) SEQUENCE DESCRIPTION: SEQ ID NO:27:

CGCTTCTCCC GGATTCTGGA GTCC                                              24

( 2 ) INFORMATION FOR SEQ ID NO:28:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 4, CLONE DT110,
            POSITION 257

( x i ) SEQUENCE DESCRIPTION: SEQ ID NO:28:

TTCCCATCAG CCGCCCAAAC CTAA        24

( 2 ) INFORMATION FOR SEQ ID NO:29:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 5, CLONE VB12A1,
            POSITION 199*

( x i ) SEQUENCE DESCRIPTION: SEQ ID NO:29:

AGCTCTGAGC TGAATGTGAA CGCC        24

( 2 ) INFORMATION FOR SEQ ID NO:30:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: THE V BETA 6, CLONE ATL12.2,
            POSITION 117, THE 18TH NUCLEOTIDE CORRESPONDS TO
            MISMATCHES INTRODUCED RELATIVE TO THE NATURAL SEQUENCE ( x i ) SEQUENCE DESCRIPTION: SEQ ID NO:30:

TCTCAGGTGT GATCCAAATT CGGG        24

( 2 ) INFORMATION FOR SEQ ID NO:31:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 7, CLONE PL4.9,
            POSITION 169*

( x i ) SEQUENCE DESCRIPTION: SEQ ID NO:31:

CCTGAATGCC CCAACAGCTC TCTC        24

( 2 ) INFORMATION FOR SEQ ID NO:32:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( D ) OTHER INFORMATION: TYPE V BETA 8, CLONE PH11,
          POSITION 170

( x i ) SEQUENCE DESCRIPTION: SEQ ID NO:32:

CCATGATGCG GGGACTGGAG TTGC                                    24

( 2 ) INFORMATION FOR SEQ ID NO:33:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( D ) OTHER INFORMATION: TYPE V BETA 9, CLONE PL2.6,
          POSITION 201*

( x i ) SEQUENCE DESCRIPTION: SEQ ID NO:33:

TTCCCTGGAG CTTGGTGACT CTGC                                    24

( 2 ) INFORMATION FOR SEQ ID NO:34:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( D ) OTHER INFORMATION: TYPE V BETA 10, CLONE ATL12-1,
          POSITIN 299

( x i ) SEQUENCE DESCRIPTION: SEQ ID NO:34:

CCACGGAGTC AGGGGACACA GCAC                                    24

( 2 ) INFORMATION FOR SEQ ID NO:35:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( D ) OTHER INFORMATION: TYPE V BETA 11, CLONE PL3.12,
          POSITION 297

( x i ) SEQUENCE DESCRIPTION: SEQ ID NO:35:

TGCCAGGCCC TCACATACCT CTCA                                    24

( 2 ) INFORMATION FOR SEQ ID NO:36:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 12, CLONE VBPH27,
            POSITION 109*, THE 14TH AND 23RD NUCLEOTIDES
            CORRESPOND TO MISMATCHES INTRODUCED RELATIVE TO THE
            NATURAL SEQUENCE ( x i ) SEQUENCE DESCRIPTION: SEQ ID NO:36:

TGTCACCAGA CTGGGAACCA CCAC            24

( 2 ) INFORMATION FOR SEQ ID NO:37:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 13, CLONE CEM-VB1,
            POSITION 116, THE 7TH AND 12TH NUCLEOTIDES
            CORRESPOND TO MISMATCHES INTRODUCED RELATIVE TO THE
            NATURAL SEQUENCE ( x i ) SEQUENCE DESCRIPTION: SEQ ID NO:37:

CACTGCGGTG TACCCAGGAT ATGA            24

( 2 ) INFORMATION FOR SEQ ID NO:38:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 14, CLONE VBPH21,
            POSITION 175, THE 6TH AND 20TH NUCLEOTIDES
            CORRESPOND TO MISMATCHES INTRODUCED RELATIVE TO THE
            NATURAL SEQUENCE ( x i ) SEQUENCE DESCRIPTION: SEQ ID NO:38:

GGGCTCGGCT TAAGGCAGAC CTAC            24

( 2 ) INFORMATION FOR SEQ ID NO:39:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:

( D ) OTHER INFORMATION: TYPE V BETA 15, CLONE ALT2-1,
POSITIN 262

( x i ) SEQUENCE DESCRIPTION: SEQ ID NO:39:

CAGGCACAGG CTAAATTCTC CCTG                                          24

( 2 ) INFORMATION FOR SEQ ID NO:40:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 16, CLONE HBP42,
POSITION 192*

( x i ) SEQUENCE DESCRIPTION: SEQ ID NO:40:

GCCTGCAGAA CTGGAGGATT CTGG                                          24

( 2 ) INFORMATION FOR SEQ ID NO:41:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 17, CLONE VBPH29,
POSITION 254

( x i ) SEQUENCE DESCRIPTION: SEQ ID NO:41:

CTGCTGAATT TCCCAAAGAG GGCC                                          24

( 2 ) INFORMATION FOR SEQ ID NO:42:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 18, CLONE HUT102,
POSITION 173*

( x i ) SEQUENCE DESCRIPTION: SEQ ID NO:42:

TGCCCCAGAA TCTCTCAGCC TCCA                                          24

( 2 ) INFORMATION FOR SEQ ID NO:43:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:

(D) OTHER INFORMATION: TYPE V BETA 19, CLONE HBVT02, POSITION 279

(x i) SEQUENCE DESCRIPTION: SEQ ID NO:43:

TCCTCTCACT GTGACATCGG CCCA     24

(2) INFORMATION FOR SEQ ID NO:44:

(i) SEQUENCE CHARACTERISTICS:
      (A) LENGTH: 24
      (B) TYPE: NUCLEOTIDE
      (C) STRANDEDNESS: SINGLE
      (D) TOPOLOGY: LINEAR (i i) MOLECULE TYPE: OLIGONUCLEOTIDE (i x) FEATURE:
      (A) NAME/KEY:
      (D) OTHER INFORMATION: TYPE V BETA 20, CLONE HBVT72, POSITION 274

(x i) SEQUENCE DESCRIPTION: SEQ ID NO:44:

TCTCAATGCC CCAAGAACGC ACCC     24

(2) INFORMATION FOR SEQ ID NO:45:

(i) SEQUENCE CHARACTERISTICS:
      (A) LENGTH: 24
      (B) TYPE: NUCLEOTIDE
      (C) STRANDEDNESS: SINGLE
      (D) TOPOLOGY: LINEAR (i i) MOLECULE TYPE: OLIGONUCLEOTIDE (i x) FEATURE:
      (A) NAME/KEY:
      (D) OTHER INFORMATION: TYPE V BETA w21, CLONE IGRb011, POSITION 318, THE 13TH AND 20TH NUCLEOTIDES CORRESPOND TO MISMATCHES INTRODUCED RELATIVE TO THE NATURAL SEQUENCE (x i) SEQUENCE DESCRIPTION: SEQ ID NO:45:

TCCAACCTGC AAGGCTTGAC GACT     24

(2) INFORMATION FOR SEQ ID NO:46:

(i) SEQUENCE CHARACTERISTICS:
      (A) LENGTH: 24
      (B) TYPE: NUCLEOTIDE
      (C) STRANDEDNESS: SINGLE
      (D) TOPOLOGY: LINEAR (i i) MOLECULE TYPE: OLIGONUCLEOTIDE (i x) FEATURE:
      (A) NAME/KEY:
      (D) OTHER INFORMATION: TYPE V BETA w22, CLONE IGRb03, POSITION 110

(x i) SEQUENCE DESCRIPTION: SEQ ID NO:46:

AAGTGATCTT GCGCTGTGTC CCCA     24

(2) INFORMATION FOR SEQ ID NO:47:

(i) SEQUENCE CHARACTERISTICS:
      (A) LENGTH: 24
      (B) TYPE: NUCLEOTIDE
      (C) STRANDEDNESS: SINGLE
      (D) TOPOLOGY: LINEAR (i i) MOLECULE TYPE: OLIGONUCLEOTIDE ( i x ) FEATURE:
  ( A ) NAME/KEY:
  ( D ) OTHER INFORMATION: TYPE V BETA w23, CLONE IGRa04,
    POSITION 155*

( x i ) SEQUENCE DESCRIPTION: SEQ ID NO:47:

GCAGGGTCCA GGTCAGGACC CCCA                   24

( 2 ) INFORMATION FOR SEQ ID NO:48:

( i ) SEQUENCE CHARACTERISTICS:
  ( A ) LENGTH: 24
  ( B ) TYPE: NUCLEOTIDE
  ( C ) STRANDEDNESS: SINGLE
  ( D ) TOPOLOGY: LINEAR ( i i ) MOLECULE TYPE: OLIGONUCLEOTIDE ( i x ) FEATURE:
  ( A ) NAME/KEY:
  ( D ) OTHER INFORMATION: TYPE V BETA w24, CLONE IGRa05,
    POSITION 95

( x i ) SEQUENCE DESCRIPTION: SEQ ID NO:48:

CCCAGTTTGG AAAGCCAGTG ACCC                   24

( 2 ) INFORMATION FOR SEQ ID NO:49:

( i ) SEQUENCE CHARACTERISTICS:
  ( A ) LENGTH: 24
  ( B ) TYPE: NUCLEOTIDE
  ( C ) STRANDEDNESS: SINGLE
  ( D ) TOPOLOGY: LINEAR ( i i ) MOLECULE TYPE: OLIGONUCLEOTIDE ( i x ) FEATURE:
  ( A ) NAME/KEY:
  ( D ) OTHER INFORMATION: TYPE C BETA A, POSITION 71

( x i ) SEQUENCE DESCRIPTION: SEQ ID NO:49:

GGTGTGGGAG AATTCTGCTT CTGA                   24

( 2 ) INFORMATION FOR SEQ ID NO:50:

( i ) SEQUENCE CHARACTERISTICS:
  ( A ) LENGTH: 24
  ( B ) TYPE: NUCLEOTIDE
  ( C ) STRANDEDNESS: SINGLE
  ( D ) TOPOLOGY: LINEAR ( i i ) MOLECULE TYPE: OLIGONUCLEOTIDE ( i x ) FEATURE:
  ( A ) NAME/KEY:
  ( D ) OTHER INFORMATION: TYPE C BETA B, POSITION 135

( x i ) SEQUENCE DESCRIPTION: SEQ ID NO:50:

ACCAGCTCAG CTCCGCGGGG TCGG                   24

( 2 ) INFORMATION FOR SEQ ID NO:51:

( i ) SEQUENCE CHARACTERISTICS:
  ( A ) LENGTH: 19
  ( B ) TYPE: NUCLEOTIDE
  ( C ) STRANDEDNESS: SINGLE
  ( D ) TOPOLOGY: LINEAR ( i i ) MOLECULE TYPE: OLIGONUCLEOTIDE ( i x ) FEATURE:
  ( A ) NAME/KEY:

( D ) OTHER INFORMATION: TYPE C BETA C, POSITION 58

( x i ) SEQUENCE DESCRIPTION: SEQ ID NO:51:

TCTGCTTCTG ATGGCTCAA                                                          19

( 2 ) INFORMATION FOR SEQ ID NO:52:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE ACT 1, CLONE BETA-ACTIN,
            POSITION 1161

( x i ) SEQUENCE DESCRIPTION: SEQ ID NO:52:

ATTTGCGGTG GACGATGGAG GGGC                                                    24

( 2 ) INFORMATION FOR SEQ ID NO:53:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE ACT 2, CLONE BETA-ACTIN
            POSITION 261

( x i ) SEQUENCE DESCRIPTION: SEQ ID NO:53:

GGCATCGTCA CCAACTGGGA CGAC                                                    24

( 2 ) INFORMATION FOR SEQ ID NO:54:

( i ) SEQUENCE CHARACTERISTICS:
        ( A ) LENGTH: 19
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE ACT 3, CLONE BETA ACTIN,
            POSITION 642

( x i ) SEQUENCE DESCRIPTION: SEQ ID NO:54:

ACCACCACGG CGGAGCGGG                                                          19

( 2 ) INFORMATION FOR SEQ ID NO:55:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE C ALPHA E, POSITION 201

( x i ) SEQUENCE DESCRIPTION: SEQ ID NO:55:

GTTGCTCCAG GCCGCGGCAC TGTT                                                                          2 4

( 2 ) INFORMATION FOR SEQ ID NO:56:

( i ) SEQUENCE CHARACTERISTICS:
       ( A ) LENGTH: 24
       ( B ) TYPE: NUCLEOTIDE
       ( C ) STRANDEDNESS: SINGLE
       ( D ) TOPOLOGY: LINEAR ( i i ) MOLECULE TYPE: OLIGONUCLEOTIDE ( i x ) FEATURE:
       ( A ) NAME/KEY:
       ( D ) OTHER INFORMATION: TYPE C ALPHA J, POSITION 12

( x i ) SEQUENCE DESCRIPTION: SEQ ID NO:56:

CCCTGACCCT GCCGTGTACC AGCT                                                                          2 4

( 2 ) INFORMATION FOR SEQ ID NO:57:

( i ) SEQUENCE CHARACTERISTICS:
       ( A ) LENGTH: 19
       ( B ) TYPE: NUCLEOTIDE
       ( C ) STRANDEDNESS: SINGLE
       ( D ) TOPOLOGY: LINEAR ( i i ) MOLECULE TYPE: OLIGONUCLEOTIDE ( i x ) FEATURE:
       ( A ) NAME/KEY:
       ( D ) OTHER INFORMATION: TYPE C ALPHA C, POSITION 57

( x i ) SEQUENCE DESCRIPTION: SEQ ID NO:57:

GTCACTGGAT TTAGAGTCT                                                                                1 9

( 2 ) INFORMATION FOR SEQ ID NO: 58:

( i ) SEQUENCE CHARACTERISTICS:
       ( A ) LENGTH: 24
       ( B ) TYPE: NUCLEOTIDE
       ( C ) STRANDEDNESS: SINGLE
       ( D ) TOPOLOGY: LINEAR ( i i ) MOLECULE TYPE: OLIGONUCLEOTIDE ( i x ) FEATURE:
       ( A ) NAME/KEY:
       ( D ) OTHER INFORMATION: TYPE V Alpha 1, THE 6TH AND 23RD
           NUCLEOTIDES CORRESPOND TO MISMATCHES INTRODUCED RELATIVE
           TO THE NATURAL SEQUENCE ( x i ) SEQUENCE DESCRIPTION: SEQ ID NO:58:

GGCATTAACG GTTTGAGGC TGGA                                                                           2 4

( 2 ) INFORMATION FOR SEQ ID NO: 59:

( i ) SEQUENCE CHARACTERISTICS:
       ( A ) LENGTH: 24
       ( B ) TYPE: NUCLEOTIDE
       ( C ) STRANDEDNESS: SINGLE
       ( D ) TOPOLOGY: LINEAR ( i i ) MOLECULE TYPE: OLIGONUCLEOTIDE ( i x ) FEATURE:
       ( A ) NAME/KEY:
       ( D ) OTHER INFORMATION: TYPE V Alpha 2, THE 24TH NUCLEOTIDE
           CORRESPONDS TO A MISMATCH INTRODUCED RELATIVE TO THE
           NATURAL SEQUENCE ( x i ) SEQUENCE DESCRIPTION: SEQ ID NO:59:

CAGTGTTCCA GAGGGAGCCA TTGC 24

( 2 ) INFORMATION FOR SEQ ID NO: 60:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha 3

( x i ) SEQUENCE DESCRIPTION: SEQ ID NO:60:

CCGGGCAGCA GACACTGCTT CTTA 24

( 2 ) INFORMATION FOR SEQ ID NO: 61:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha 4

( x i ) SEQUENCE DESCRIPTION: SEQ ID NO:61:

TTGGTATCGA CAGCTTCCCT CCCA 24

( 2 ) INFORMATION FOR SEQ ID NO: 62:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha 5

( x i ) SEQUENCE DESCRIPTION: SEQ ID NO:62:

CGGCCACCCT GACCTGCAAC TATA 24

( 2 ) INFORMATION FOR SEQ ID NO: 63:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha 6

( x i ) SEQUENCE DESCRIPTION: SEQ ID NO:63:

TCCGCCAACC TTGTCATCTC CGCT 24

( 2 ) INFORMATION FOR SEQ ID NO: 64:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( D ) OTHER INFORMATION: TYPE V Alpha 7, THE 9TH AND 15TH
      NUCLEOTIDES CORRESPOND TO MISMATCHES INTRODUCED RELATIVE
      TO THE NATURAL SEQUENCE ( x i ) SEQUENCE DESCRIPTION: SEQ ID NO:64:

GCAACATGCT GGCGGAGCAC CCAC    24

( 2 ) INFORMATION FOR SEQ ID NO: 65:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( D ) OTHER INFORMATION: TYPE V Alpha 8

( x i ) SEQUENCE DESCRIPTION: SEQ ID NO:65:

CATTCGTTCA AATGTGGGCA AAAG    24

( 2 ) INFORMATION FOR SEQ ID NO: 66:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( D ) OTHER INFORMATION: TYPE V Alpha 9, THE 22ND NUCLEOTIDE
      CORRESPONDS TO A MISMATCH INTRODUCED RELATIVE TO THE
      NATURAL SEQUENCE ( x i ) SEQUENCE DESCRIPTION: SEQ ID NO:66:

CCAGTACTCC AGACAACGCC TGCA    24

( 2 ) INFORMATION FOR SEQ ID NO: 67:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( D ) OTHER INFORMATION: TYPE V Alpha 10

( x i ) SEQUENCE DESCRIPTION: SEQ ID NO:67:

CACTGCGGCC CAGCCTGGTG ATAC    24

( 2 ) INFORMATION FOR SEQ ID NO: 68:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( D ) OTHER INFORMATION: TYPE V Alpha 11

( x i ) SEQUENCE DESCRIPTION: SEQ ID NO:68:

CGCTGCTCAT CCTCCAGGTG CGGG          24

( 2 ) INFORMATION FOR SEQ ID NO: 69:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( D ) OTHER INFORMATION: TYPE V Alpha 12

( x i ) SEQUENCE DESCRIPTION: SEQ ID NO:69:

TCGTCGGAAC TCTTTTGATG AGCA          24

( 2 ) INFORMATION FOR SEQ ID NO: 70:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( D ) OTHER INFORMATION: TYPE V Alpha 13

( x i ) SEQUENCE DESCRIPTION: SEQ ID NO:70:

TTCATCAAAA CCCTTGGGGA CAGC          24

( 2 ) INFORMATION FOR SEQ ID NO: 71:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( D ) OTHER INFORMATION: TYPE V Alpha 14

( x i ) SEQUENCE DESCRIPTION: SEQ ID NO:71:

CCCAGCAGGC AGATGATTCT CGTT          24

( 2 ) INFORMATION FOR SEQ ID NO: 72:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( D ) OTHER INFORMATION: TYPE V Alpha 15, THE 12TH NUCLEOTIDE
        CORRESPONDS TO A MISMATCH INTRODUCED RELATIVE TO THE
        NATURAL SEQUENCE ( x i ) SEQUENCE DESCRIPTION: SEQ ID NO:72:

TTGCAGACAC CGAGACTGGG GACT     24

( 2 ) INFORMATION FOR SEQ ID NO: 73:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( D ) OTHER INFORMATION: TYPE V Alpha 16

( x i ) SEQUENCE DESCRIPTION: SEQ ID NO:73:

TCAACGTTGC TGAAGGGAAT CCTC     24

( 2 ) INFORMATION FOR SEQ ID NO: 74:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( D ) OTHER INFORMATION: TYPE V Alpha 17, THE 12TH NUCLEOTIDE
        CORRESPONDS TO A MISMATCH INTRODUCED RELATIVE TO THE
        NATURAL SEQUENCE ( x i ) SEQUENCE DESCRIPTION: SEQ ID NO:74:

TGGGAAAGGC CGTGCATTAT TGAT     24

( 2 ) INFORMATION FOR SEQ ID NO: 75:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( D ) OTHER INFORMATION: TYPE V Alpha 18

( x i ) SEQUENCE DESCRIPTION: SEQ ID NO:75:

CAGCACCAAT TTCACCTGCA GCTT     24

( 2 ) INFORMATION FOR SEQ ID NO: 76:

( i, ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( D ) OTHER INFORMATION: TYPE V Alpha 19

( x i ) SEQUENCE DESCRIPTION: SEQ ID NO:76:

ACACTGGCTG CAACAGCATC CAGG      24

( 2 ) INFORMATION FOR SEQ ID NO: 77:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha 20

( x i ) SEQUENCE DESCRIPTION: SEQ ID NO:77:

TCCCTGTTTA TCCCTGCCGA CAGA      24

( 2 ) INFORMATION FOR SEQ ID NO: 78:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha 21

( x i ) SEQUENCE DESCRIPTION: SEQ ID NO:78:

AGCAAAATTC ACCATCCCTG AGCG      24

( 2 ) INFORMATION FOR SEQ ID NO: 79:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha 22

( x i ) SEQUENCE DESCRIPTION: SEQ ID NO:79:

CCTGAAAGCC ACGAAGGCTG ATGA      24

( 2 ) INFORMATION FOR SEQ ID NO: 80:

( i ) SEQUENCE CHARACTERISTICS:
        ( A ) LENGTH: 24
        ( B ) TYPE: NUCLEOTIDE
        ( C ) STRANDEDNESS: SINGLE ( D ) TOPOLOGY: LINEAR ( i i ) MOLECULE TYPE: OLIGONUCLEOTIDE ( i x ) FEATURE:
            ( A ) NAME/KEY:
            ( D ) OTHER INFORMATION: TYPE V Alpha w23

( x i ) SEQUENCE DESCRIPTION: SEQ ID NO:80:

TGCCTCGCTG GATAAATCAT CAGG 24

( 2 ) INFORMATION FOR SEQ ID NO: 81:

( i ) SEQUENCE CHARACTERISTICS:
            ( A ) LENGTH: 24
            ( B ) TYPE: NUCLEOTIDE
            ( C ) STRANDEDNESS: SINGLE
            ( D ) TOPOLOGY: LINEAR ( i i ) MOLECULE TYPE: OLIGONUCLEOTIDE ( i x ) FEATURE:
            ( A ) NAME/KEY:
            ( D ) OTHER INFORMATION: TYPE V Alpha w24, THE 21ST NUCLEOTIDE
                CORRESPONDS TO A MISMATCH INTRODUCED RELATIVE TO THE
                NATURAL SEQUENCE ( x i ) SEQUENCE DESCRIPTION: SEQ ID NO:81:

CTGGATGCAG ACACAAAGCA GAGC 24

( 2 ) INFORMATION FOR SEQ ID NO: 82:

( i ) SEQUENCE CHARACTERISTICS:
            ( A ) LENGTH: 24
            ( B ) TYPE: NUCLEOTIDE
            ( C ) STRANDEDNESS: SINGLE
            ( D ) TOPOLOGY: LINEAR ( i i ) MOLECULE TYPE: OLIGONUCLEOTIDE ( i x ) FEATURE:
            ( A ) NAME/KEY:
            ( D ) OTHER INFORMATION: TYPE V Alpha w25, THE 7TH AND 17TH
                NUCLEOTIDES CORRESPOND TO MISMATCHES INTRODUCED RELATIVE
                TO THE NATURAL SEQUENCE ( x i ) SEQUENCE DESCRIPTION:SEQ ID NO:82:

TGGCTACGGT ACAAGCCGGA CCCT 24

( 2 ) INFORMATION FOR SEQ ID NO: 83:

( i ) SEQUENCE CHARACTERISTICS:
            ( A ) LENGTH: 24
            ( B ) TYPE: NUCLEOTIDE
            ( C ) STRANDEDNESS: SINGLE
            ( D ) TOPOLOGY: LINEAR ( i i ) MOLECULE TYPE: OLIGONUCLEOTIDE ( i x ) FEATURE:
            ( A ) NAME/KEY:
            ( D ) OTHER INFORMATION: TYPE V Alpha w26, THE 4TH AND 20TH
                NUCLEOTIDES CORRESPOND TO MISMATCHES INTRODUCED RELATIVE
                TO THE NATURAL SEQUENCE ( x i ) SEQUENCE DESCRIPTION: SEQ ID NO:83:

AGCGCAGCCA TGCAGGCATG TACC 24

( 2 ) INFORMATION FOR SEQ ID NO: 84:

( i ) SEQUENCE CHARACTERISTICS:
            ( A ) LENGTH: 24

-continued (B) TYPE: NUCLEOTIDE
            (C) STRANDEDNESS: SINGLE
            (D) TOPOLOGY: LINEAR (ii) MOLECULE TYPE: OLIGONUCLEOTIDE (ix) FEATURE:
            (A) NAME/KEY:
            (D) OTHER INFORMATION: TYPE V Alpha w27

(xi) SEQUENCE DESCRIPTION: SEQ ID NO:84:

AAGCCCGTCT CAGCACCCTC CACA                                                              24

(2) INFORMATION FOR SEQ ID NO: 85:

(i) SEQUENCE CHARACTERISTICS:
            (A) LENGTH: 24
            (B) TYPE: NUCLEOTIDE
            (C) STRANDEDNESS: SINGLE
            (D) TOPOLOGY: LINEAR (ii) MOLECULE TYPE: OLIGONUCLEOTIDE (ix) FEATURE:
            (A) NAME/KEY:
            (D) OTHER INFORMATION: TYPE V Alpha w28, THE 8TH AND 15TH
                    NUCLEOTIDES CORRESPOND TO MISMATCHES INTRODUCED RELATIVE
                    TO THE NATURAL SEQUENCE (xi) SEQUENCE DESCRIPTION: SEQ ID NO:85:

TGGTTGTGCA CGAGCGAGAC ACTG                                                              24

(2) INFORMATION FOR SEQ ID NO: 86:

(i) SEQUENCE CHARACTERISTICS:
            (A) LENGTH: 24
            (B) TYPE: NUCLEOTIDE
            (C) STRANDEDNESS: SINGLE
            (D) TOPOLOGY: LINEAR (ii) MOLECULE TYPE: OLIGONUCLEOTIDE (ix) FEATURE:
            (A) NAME/KEY:
            (D) OTHER INFORMATION: TYPE V Alpha w29

(xi) SEQUENCE DESCRIPTION: SEQ ID NO:86:

GAAGGGTGGA GAACAGATGC GTCG                                                              24

(2) INFORMATION FOR SEQ ID NO: 87:

(i) SEQUENCE CHARACTERISTICS:
            (A) LENGTH: 24
            (B) TYPE: NUCLEOTIDE
            (C) STRANDEDNESS: SINGLE
            (D) TOPOLOGY: LINEAR (ii) MOLECULE TYPE: OLIGONUCLEOTIDE (ix) FEATURE:
            (A) NAME/KEY:
            (D) OTHER INFORMATION: TYPE C Alpha A (xi) SEQUENCE DESCRIPTION: SEQ ID NO:87:

ATACACATCA GAATTCTTAC TTTG                                                              24

(2) INFORMATION FOR SEQ ID NO: 88:

(i) SEQUENCE CHARACTERISTICS:
            (A) LENGTH: 24
            (B) TYPE: NUCLEOTIDE
            (C) STRANDEDNESS: SINGLE (D) TOPOLOGY: LINEAR (ii) MOLECULE TYPE: OLIGONUCLEOTIDE (ix) FEATURE:
 (A) NAME/KEY:
 (D) OTHER INFORMATION: TYPE C Alpha B (xi) SEQUENCE DESCRIPTION: SEQ ID NO:88:

GTTGCTCCAG GCCGCGGCAC TGTT  24